United States Patent
Giladi et al.

(10) Patent No.: US 10,392,617 B2
(45) Date of Patent: Aug. 27, 2019

(54) **MIR-122* AS AN ACTIVE MICRO-RNA, COMPOSITIONS COMPRISING THE SAME AND USES THEREOF**

(71) Applicant: HADASIT MEDICAL RESEARCH SERVICES AND DEVELOPMENT LTD., Jerusalem (IL)

(72) Inventors: Hilla Giladi, Mevaseret Zion (IL); Alina Simerzin, Jerusalem (IL); Yael Hantz, Jerusalem (IL); Sagit Arbel Alon, Reut (IL); Eithan Galun, Har-Adar (IL)

(73) Assignee: HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 0 days.

(21) Appl. No.: 15/109,879

(22) PCT Filed: Jan. 6, 2015

(86) PCT No.: PCT/IL2015/050024
§ 371 (c)(1),
(2) Date: Jul. 6, 2016

(87) PCT Pub. No.: WO2015/104706
PCT Pub. Date: Jul. 16, 2015

(65) Prior Publication Data
US 2016/0333344 A1   Nov. 17, 2016

Related U.S. Application Data

(60) Provisional application No. 61/924,719, filed on Jan. 8, 2014.

(51) Int. Cl.
| | | |
|---|---|---|
| *C12N 15/11* | (2006.01) | |
| *C12N 15/113* | (2010.01) | |
| *A61K 31/7105* | (2006.01) | |
| *A61K 45/06* | (2006.01) | |
| *A61K 31/713* | (2006.01) | |
| *A61K 31/7088* | (2006.01) | |

(52) U.S. Cl.
CPC ........ *C12N 15/113* (2013.01); *A61K 31/7088* (2013.01); *A61K 31/713* (2013.01); *A61K 31/7105* (2013.01); *A61K 45/06* (2013.01); *C12N 2310/141* (2013.01); *C12N 2320/30* (2013.01); *C12N 2320/31* (2013.01)

(58) Field of Classification Search
None
See application file for complete search history.

(56) References Cited

U.S. PATENT DOCUMENTS 7,232,806 B2   6/2007   Tuschl et al.
2009/0143326 A1*  6/2009   Obad .................... C12N 15/111
                                              514/44 R

FOREIGN PATENT DOCUMENTS

CN   103088061 A   5/2013

OTHER PUBLICATIONS

Kessis et al., Human papillomavirus 16 E6 expression disrupts the p53-mediated cellular response to DNA damage, 1993, PNAS, vol. 90, pp. 3988-3992.*
Chelliserrykattil et al., Evolution of a T7 RNA polymerase variant that transcribes 2'-O-methyl RNA, 2004, Nature Biotechnology, vol. 22, pp. 1155-1160.*
Gebert et al., Supplementary information of Nucleic Acids Research, 2014, vol. 42, pp. 609-621.*
"Stem-loop sequence hsa-mir-122", miRNA Entry for MI0000442, accessed and retrieved from www.mirbase.org on Apr. 24, 2018.*
Pradere et al., Angewandte Communications International Edition, 2013, 52:12028-12032.*
Kitahara et al., Biology of Reproduction, 2013, 89:1-10.*
Lei et al., PLoS One, 2013, 8:e60369.*
Nimmo et al., Developmental Cell, 2013, 26:237-249.*
Goedeke et al., Molecular and Cellular Biology, 2013, 33:2339-2352.*
Squadrito et al., Cell Reports, 2012, 1:141-154.*
Li et al., European Journal of Cancer, 2013, 49:2596-2607.*
Hao et al., FEBS Letters, 2011, 585:207-213.*
Kwon et al., Apoptosis, 2013, 18:896-909.*
Henry et al., BBRC, 2010, 403:120-125.*
Lo et al., PLoS One, 2013, 8:e75628.*
Kos et al., PLoS One, 2012, 7:e31022.*
Chen et al., Neuron, 2011, 69:721-735.*
Mo et al., Oncology Letters, 2013, 6:617-623.*
Hashiguchi et al., International Journal of Oncology, 2012, 40:1477-1482.*
Guo et al., PLoS One, 2010, 5:311387.*
Gatfield et al., Genes & Development, 2009, 23:1313-1326.*
Bai et al., (2009) MicroRNA-122 inhibits tumorigenic properties of hepatocellular carcinoma cells and sensitizes these cells to sorafenib. The journal of biological chemistry 284:32015-32027.
Bartel, (2004) MicroRNAs: genomics, biogenesis, mechanism, and function. Cell 116:281-297.
Burchard et al., (2010) microRNA-122 as a regulator of mitochondrial metabolic gene network in hepatocellular carcinoma. Molecular Systems Biology 6:402; 12 pages.
Butz et al., (2003) siRNA targeting of the viral E6 oncogene efficiently kills human papillomavirus-positive cancer cells. Oncogene 22:5938-5945.

(Continued)

*Primary Examiner* — Dana H Shin
(74) *Attorney, Agent, or Firm* — J. A. Lindeman & Co., PLLC; Sulay Jhaveri; Jeffrey Lindeman

(57) ABSTRACT

The present invention provides miR-122* as a functional microRNA molecule, compositions comprising the same and uses thereof for treatment of various conditions, such as, cancer. Further provided are methods for increasing the expression, stability and/or activity of p53 in a target cell or method for inducing cancer cell death, the methods comprising introducing into the cell a miR-122* polynucleotide molecule or a vector expressing or encoding the same.

12 Claims, 17 Drawing Sheets

Specification includes a Sequence Listing.

(56) References Cited

OTHER PUBLICATIONS

Chang et al., (2004) miR-122, a mammalian liver-specific microRNA, is processed from her mRNA and may downregulate the high affinity cationic amino acid transporter CAT-1. RNA Biol 1: 106-113.
Chang et al., (2010) Highly potent and specific siRNAs against E6 or E7 genes of HPV16- or HPV18-infected cervical cancers. 17:827-836.
Chen et al., (1993) Mapping of the p53 and mdm-2 interaction domains. Molecular and Cellular Biology 13:4107-4114.
Coulouarn et al., (2009) Loss of miR-122 expression in liver cancer correlates with suppression of the hepatic phenotype and gain of metastatic properties. Oncogene 28:3526-3536.
Elmén et al., (2008) Antagonism of microRNA-122 in mice by systemically administered LNA-antimiR leads to up-regulation of a large set of predicted target mRNAs in the liver. Nucleic Acids Research 36:1153-1162.
Elmén et al., (2008) LNA-mediated microRNA silencing in non-human primates. Nature 452: 896-899.
Esau et al., (2006) miR-122 regulation of lipid metabolism revealed by in vivo antisense targeting. Cell Metab. 3: 87-98.
Esau, (2008) Inhibition of microRNA with antisense oligonucleotides. Methods 44:55-60.
Fornari et al., (2009) MiR-122/cyclin G1 interaction modulates p53 activity and affects doxorubicin sensitivity of human hepatocarcinoma cells. Cancer Res 69(14):5761-5767.
Gebert et al., (2014) Miravirsen (SPC3649) can inhibit the biogenesis of miR-122. Nucleic Acids Research 42: 609-621.
Haupt et al., (1997) Mdm2 promotes the rapid degradation of p53. Nature 387:296-299.
Hoffman et al., (2013) miR-661 downregulates both Mdm2 and Mdm4 to activate p53. Cell Death Differ 21:302-309.
Hsu et al., (2012) Essential metabolic, anti-inflammatory, and anti-tumorigenic functions of miR-122 in liver. J. Clin. Invest. 122:2871-2883.
Hsu et al., (2013) Hepatic Loss of miR-122 Predisposes Mice to Hepatobiliary Cyst and Hepatocellular Carcinoma upon Diethylnitrosamine Exposure. The American Journal of Pathology 183:1719-1730.
Janssen et al., (2013) Treatment of HCV infection by targeting microRNA. N Engl J Med 368:1685-1694.
Koivusalo et al., (2005) Chemotherapy compounds in cervical cancer cells primed by reconstitution of p53 function after short interfering RNA-mediated degradation of human papillomavirus 18 E6 mRNA: opposite effect of siRNA in combination with different drugs. Mol. Pharmacol. 68:372-382.
Komarov et al., (1999) A chemical inhibitor of p53 that protects mice from the side effects of cancer therapy. Science 285:1733-1737.
Krützfeldt et al., (2005) Silencing of microRNAs in vivo with 'antagomirs'. Nature 438:685-689.
Krützfeldt et al., (2007) Specificity, duplex degradation and subcellular localization of antagomirs. Nucleic Acids Research 35:2885-2892.
Kutay et al., (2006) Downregulation of miR-122 in the rodent and human hepatocellular carcinomas. J. Cell. Biochem. 99:671-678.
Lagos-Quintana et al., (2002) Identification of tissue-specific microRNAs from mouse. Curr. Biol. 12:735-739.
Lewis et al., (2005) Conserved seed pairing, often flanked by adenosines, indicates that thousands of human genes are microRNA targets. Cell 120:15-20.
Liu et al., (1999) Hydrodynamics-based transfection in animals by systemic administration of plasmid DNA. Gene Therapy 6:1258-1266.
Ma et al., (2010) Expression of miR-122 mediated by adenoviral vector induces apoptosis and cell cycle arrest of cancer cells. Cancer Biol Ther; 9(7):554-561.
Mauad et al., (1994) Mice with homozygous disruption of the mdr2 Pglycoprotein gene. A novel animal model for studies of nonsuppurative inflammatory cholangitis and hepatocarcinogenesis. The American Journal of Pathology 145:1237-1245.
Moody et al., (2010) Human papillomavirus oncoproteins: pathways to transformation. Nat Rev Cancer 10: 550-560.
Nassirpour et al., (2013) miR-122 regulates tumorigenesis in hepatocellular carcinoma by targeting AKT3. Plos One 8:e79655; 10 pages.
Nicoletti et al., (1991) rapid and simple method for measuring thymocyte apoptosis by propidium iodide staining and flow cytometry. J. Immunol. Methods 139: 271-279.
Ørom et al., (2007) Isolation of microRNA targets using biotinylated synthetic microRNAs. Methods 43:162-165.
Picksley et aL, (1994) Immunochemical analysis of the interaction of p53 with MDM2;—fine mapping of the MDM2 binding site on p53 using synthetic peptides. Oncogene 9: 2523-2529 abstract.
Riccardi et al., (2006) Analysis of apoptosis by propidium iodide staining and flow cytometry. Nat Protoc 1:1458-1461.
Song et al., (2010) MicroRNAs control hepatocyte proliferation during liver regeneration. Hepatology 51:1735-1743.
Tsai et al., (2009) MicroRNA-122, a tumor suppressor microRNA that regulates intrahepatic metastasis of hepatocellular carcinoma. Hepatology;49(5):1571-1582.
Tsai et al., (2012) MicroRNA-122 plays a critical role in liver homeostasis and hepatocarcinogenesis. J. Clin. Invest. 122: 2884-2897.
Wu et al., (2009) miR-122 affects the viability and apoptosis of hepatocellular carcinoma cells. Scand. J. Gastroenterol. 44:1332-1339.
Yamato et al., (2008) New highly potent and specific E6 and E7 siRNAs for treatment of HPV16 positive cervical cancer. Cancer Gene Ther. 15(3):140-153.
Zeisel et al., (2013) miR-122 acts as a tumor suppressor in hepatocarcinogenesis in vivo. Journal of Hepatology 58: 821-823.
Zhang et al., (2013) miR-126 and miR-126* repress recruitment of mesenchymal stem cells and inflammatory monocytes to inhibit breast cancer metastasis. Nat. Cell Biol. 15: 284-294.
Zhou et al., (2010) miR-155 and its star-form partner miR-155* cooperatively regulate type I interferon production by human plasmacytoid dendritic cells. Blood 116: 5885-5894.
Henke et al., (2008) microRNA-122 stimulates translation of hepatitis C virus RNA. EMBO J 27(24): 3300-3310.

* cited by examiner

Fig. 3A   Mdm2   5'... TACCCAGGCTGGAGTG-CAGTGGCGTGATCTTGG...3'
         MiR-122*        3'-AUCACACUAUUACCGCAA-5'
                                            'seed'

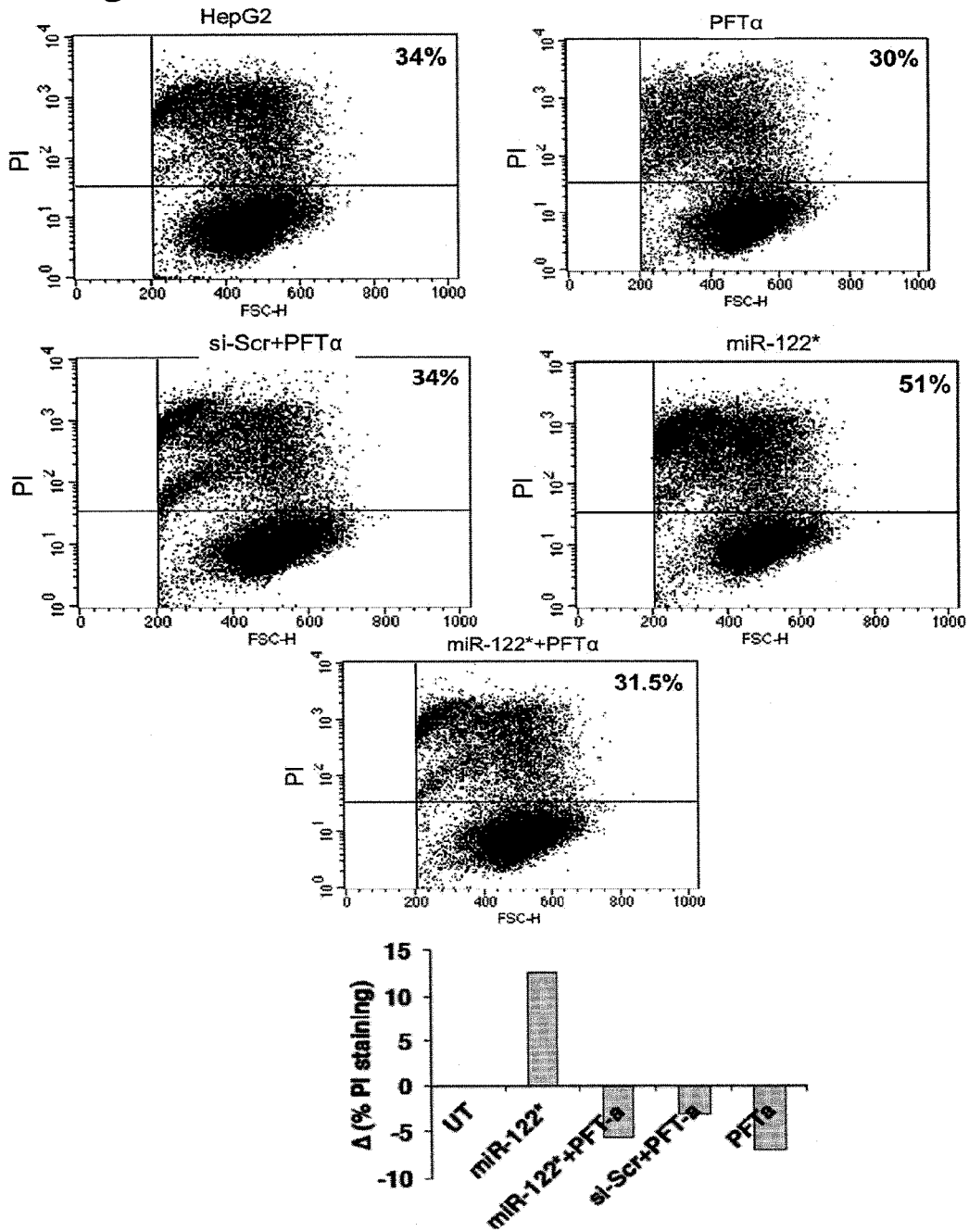

MIR-122* AS AN ACTIVE MICRO-RNA, COMPOSITIONS COMPRISING THE SAME AND USES THEREOF

The Sequence Listing submitted in text format (.txt) filed on Jul. 6, 2016, named "SequenceListing.txt", created on Jul. 5, 2016, 6.49 KB), is incorporated herein by reference.

FIELD OF THE INVENTION

The present invention provides for miR-122* as a functional microRNA, compositions comprising the same and uses thereof for the treatment of various conditions.

BACKGROUND OF THE INVENTION microRNAs (miRNAs) are short, non-coding RNA molecules, which are endogenously expressed either ubiquitously or in a tissue-specific manner, and play an important regulatory role in various cellular processes. miRNAs are of about 21 nucleotides in length that are part of a mechanism that regulate posttranscriptional gene expression. miRNAs are expressed in organisms as diverse as nematodes, fruit flies, humans and plants. In mammals, miRNAs are generally transcribed by RNA polymerase II and the resulting primary transcripts (pri-miRNAs) contain local stem-loop structures that are cleaved in the nucleus by a Drosha-DGCR8 complex. The product of this cleavage is one or more (in case of clusters) precursor miRNA (pre-miRNA). Pre-miRNAs are usually 70-90 nucleotides long with a strong stem-loop structure containing a 2 nucleotides overhang at the 3' end. The pre-miRNA is transported to the cytoplasm by Exportin-5. In the cytoplasm, the Dicer enzyme, which is an endoribonuclease of the RNase III family, further cleaves the pre-miRNA to release a 21 bp dsRNA, the miRNA duplex. The two strands of the duplex are separated from each other by the Dicer-TRBP complex and the strand that usually has thermodynamically weaker 5' end is incorporated into the RNA induced silencing complex (RISC). This strand (guide strand) is the mature miRNA. The strand which is not incorporated into RISC is called miRNA* strand (3p strand or passenger strand) and it is degraded, but occasionally both strands function as mature miRNAs. The mature miRNA guides RISC to a target site within mRNAs. If the target site has perfect complementarity to the mature miRNA, the mRNA is cleaved at a position that is located about 10 nucleotides upstream from the 3' end of the target site. After the cleavage, the RISC-mature miRNA strand complex is recycled for another activity. If the target site has lower complementarity to the mature miRNA, the mRNA will not be cleaved at the target site but the translation of the mRNA will be suppressed.

miRNA-122 is the most abundant liver specific microRNA, representing 70% of total liver miRNAs. miR-122 was recognized as a tumor suppressor miRNA. Its expression commences during gestation and attains maximal levels in the adult liver. miRNA122 plays a fundamental role in cholesterol and fatty acid metabolism. It has been shown to be required for the replication of hepatitis C virus (HCV). miR-122 was shown to be either silent or expressed at a very low level in most hepatocellular carcinomas (HCCs). U.S. Pat. No. 7,232,806 is directed to microRNA molecules and discloses miR-122 and complementary oligonucleotides thereof.

The discovery of RNA interference (siRNA) has enabled selective and highly efficient targeting of specific genes, including genes harbored by disease causing agents. RNA interference entails the introduction of short, double stranded RNA (termed small interfering RNA-siRNA) into cells which results in degradation of defined homologous target gene. Both microRNAs and siRNAs share similar machinery for recognition of their target genes.

Human papilloma viruses (HPVs) are small DNA viruses, which have been linked to a variety of epithelial cancers. Despite the introduction of screening with cervical cytologic testing (Pap test), cervical cancer remains the second most common cancer in women worldwide. Over 120 types of HPV have been identified and classified according to their tropism. A sexually transmitted subgroup consisting of several HPV types is categorized as high-risk HPVs that are responsible for over 99% of virus-mediated cervical lesions. The most prevalent high-risk types of HPV are HPV16 and HPV18, accounting for 50% and 20% of all cervical cancers, respectively.

The HPV life cycle initiates when a virus infects immature cells from the basal layers of stratified epithelia. These basal cells become exposed as a result of micro-wounds and are the only proliferating cells in normal epithelia. The HPV oncoproteins E6 and E7 are the primary viral factors responsible for initiation and progression of cervical cancer, by cooperatively acting to overcome the host cell's natural defense mechanism against uncontrolled cell division. The primary target of E7 is the Rb (retinoblastoma) tumor suppressor protein, one of the key regulators of the cell cycle. The efficient abrogation of Rb function by E7 leads to increased levels of the tumor suppressor p53, which induces the susceptibility of E7-expressing cells to apoptosis. The E6 proteins interfere with p53, abolishing its function, either by direct binding or by recruitment of cellular mechanisms for protein degradation to avoid the cellular innate response. The combined expression of E6 and E7 proteins immortalizes most types of primary cells.

Currently, pre-malignant cervical lesions are treated by local excision. This procedure has a number of disadvantages: performed only on visible lesions, destroys cervical tissue and it is associated with high recurrence rates. Advanced cancers are treated by a combination of chemotherapy and radiotherapy that have serious adverse effects.

Therefore, there is a need in the art for selective, efficient and safe treatment of various types of pre-malignant or malignant conditions. In particular, there is a need in the art for selective, efficient and safe treatment of various conditions such as, for example, HPV associated pre-malignant and malignant lesions.

SUMMARY OF THE INVENTION

The present invention in embodiments thereof provides for miR-122* polynucleotide molecule as an active microRNA molecule, capable of specifically affecting expression of target genes and having tumor suppressing activity. Further provided are compositions comprising the miR-122* molecule and/or vectors encoding or expressing the same, and uses thereof for treatment of various conditions, such as, cancer.

In some embodiments, introduction or expression of miR-122* in various cancer cells results in a dramatic induction of cell death. In further embodiments, miR-122* is capable of increasing or enhancing levels and/or activity and/or stability of p53 tumor suppressor gene both in-vitro and in-vivo. In yet further embodiments, introduction or expression of miR-122* to tumor masses results in reduction of tumor growth, in-vivo.

According to some embodiments, miR-122* may be administered or expressed in combination with one or more additional agents. In some embodiments, the additional agents are polynucleotides capable of affecting expression of additional target genes. In some exemplary embodiments, miR-122* may be introduced or expressed in a target cell or tissue in combination with additional siRNA molecule (such as an siRNA molecule directed against the E6 gene), to result in induced cell death of cancer cells, such as Human cervical cancer cells.

According to some embodiments, miR-122* comprises or consist of the nucleotide sequence as denoted by SEQ ID NO:1. In some embodiments, SEQ ID NO:1 may include one or more nucleotide modifications. In some embodiments, the miR-122* sequence comprises a seed sequence having a nucleotide sequence: 5'-3: ACGCCA (SEQ ID NO:2).

According to some embodiments, there is provided a composition comprising a polynucleotide molecule comprising the nucleotide sequence of SEQ ID NO:1, or a vector expressing or encoding for said polynucleotide. In some embodiments, there is provided a polynucleotide molecule comprising or consisting of the nucleotide sequence of SEQ ID NO:1, or a vector expressing or encoding the same.

According to some embodiments, there is provided a composition comprising a polynucleotide molecule comprising the nucleotide sequence of SEQ ID NO:2, or a vector expressing or encoding for said polynucleotide. In some embodiments, there is provided a polynucleotide molecule comprising or consisting of the nucleotide sequence of SEQ ID NO:2, or a vector expressing or encoding the same.

According to some embodiments, there is provided a method of reducing MDM2 expression or activity in a target cell, the method comprising introducing into the cell a miR-122* polynucleotide molecule or a vector expressing or encoding the same. In some embodiments, the miR-122* molecule comprises or consists of nucleotide sequence of SEQ ID NO: 1. In some embodiments, the miR-122* comprises a seed sequence having a nucleotide sequence as set forth in SEQ ID NO:2. In some embodiments, the polynucleotide molecule comprises at least one modified nucleotide. In some embodiments, the cell is a cancer cell. In some embodiments, the target cell is in-vitro. In some embodiments, the target cell is in-vivo. In some embodiments, the cell is harbored in a tissue or organism. In some exemplary embodiments, the cancer cell is of hepatic origin or cervical origin.

In some embodiments, there is provided a composition comprising miR-122* polynucleotide molecule or a vector expressing or encoding the same for reducing MDM2 expression in a target cell.

According to some embodiments, there is provided a method for elevating the expression and/or stability and/or activity of p53 in a target cell, the method comprising introducing into the cell a miR-122* polynucleotide molecule or a vector expressing or encoding the same. In some embodiments, the miR-122* molecule comprises or consists of nucleotide sequence of SEQ ID NO:1. In some embodiments, the miR-122* comprises a seed sequence having a nucleotide sequence as set forth in SEQ ID NO:2. In some embodiments, the polynucleotide molecule comprises at least one modified nucleotide. In some embodiments, the target cell is a cancer cell. In some embodiments, the target cell is in-vitro. In some embodiments, the target cell is in-vivo. In some embodiments, the target cell is harbored in a tissue or organism. In some embodiments, the cancer cell is of hepatic origin or cervical origin.

In some embodiments, there is provided a composition comprising miR-122* polynucleotide molecule or a vector expressing or encoding the same for enhancing expression and/or activity and/or stability of p53 in a target cell.

According to some embodiments, there is provided a method for inducing cell death of a cancer cell, the method comprising introducing into the cancer cell a miR-122* polynucleotide molecule or a vector expressing or encoding the same. In some embodiments, the miR-122* molecule comprises or consists of nucleotide sequence of SEQ ID NO:1. In some embodiments, the miR-122* comprises a seed sequence having a nucleotide sequence as set forth in SEQ ID NO:2. In some embodiments, the polynucleotide molecule comprises at least one modified nucleotide. In some embodiments, the target cell is in-vitro. In some embodiments, the target cell is in-vivo. In some embodiments, the cell is harbored in a tissue or organism. In some exemplary embodiments, the cancer cell is of hepatic origin or cervical origin.

In some embodiments, there is provided a composition comprising miR-122* polynucleotide molecule or a vector expressing or encoding the same for inducing cancer cell death.

According to some embodiments, there is provided a method for inhibiting or reducing growth of cancer cells, the method comprising introducing into the cell a miR-122* polynucleotide molecule or a vector expressing or encoding the same. In some embodiments, the miR-122* molecule comprises or consists of nucleotide sequence of SEQ ID NO: 1. In some embodiments, the miR-122* comprises a seed sequence having a nucleotide sequence as set forth in SEQ ID NO:2. In some embodiments, the polynucleotide molecule comprises at least one modified nucleotide. In some embodiments, the target cell is in-vitro. In some embodiments, the target cell is in-vivo. In some embodiments, the cell is harbored in a tissue or organism. In some embodiments, the cancer cell is of hepatic origin or cervical origin. In some embodiments, reducing growth comprises reducing growth rate.

In some embodiments, there is provided a composition comprising miR-122* polynucleotide molecule or a vector expressing or encoding the same for inhibiting or reducing cancer cell growth.

In some embodiments, there is provided a method for treating cancer in a subject in need thereof, the method comprising administering a miR-122* polynucleotide molecule or a vector expressing or encoding the same, thereby treating cancer in the subject. In some embodiments, the miR-122* molecule comprises or consists of the nucleotide sequence of SEQ ID NO: 1 and may further include at least one modified nucleotide. In some embodiments, the miR-122* molecule comprises a seed sequence having a nucleotide sequence as denoted by SEQ ID NO:2. In some embodiments, the cancer comprises a wild-type p53. In some embodiments, the cancer is a cervical cancer. In some embodiments, the cancer originated from viral infection. In some embodiments, wherein the viral infection is caused by Human Papiloma Virus (HPV), Hepatitis C Virus (HCV), or both. In some embodiments, the method further includes administering an agent capable of reducing expression or activity of E6 gene product, E7 gene product or both. In further embodiments, the agent is a polynucleotide molecule. In some embodiments, the polynucleotide molecule is selected from siRNA, miRNA, and antisense (AS) molecule. In additional embodiments, the agent may be administered concomitantly with the miR-122* polynucleotide molecule or the vector expressing or encoding the same. In further embodiments, the miR-122* polynucleotide molecule or the vector expressing or encoding the same and/or the agent may be formulated in one or more pharmaceutical compositions.

According to some embodiments, there is provided a method for treating cancer in a subject in need thereof, the method comprising administering a composition comprising miR-122* polynucleotide molecule or a vector expressing or encoding the same. In some embodiments, the miR-122* molecule comprises or consists of nucleotide sequence of SEQ ID NO: 1. In some embodiments, the miR-122* comprises a seed sequence having a nucleotide sequence as set forth in SEQ ID NO:2. In some embodiments, the polynucleotide molecule comprises at least one modified nucleotide. In some embodiments, the composition may further comprise one or more additional therapeutic reagents (drugs). In some embodiments, the cancer cells comprise wild-type p53. In some embodiments, the cancer is of hepatic cancer or cervical origin. In some embodiments, the cancer is head cancer or neck cancer. In some embodiments, the cancer originated from a viral infection. In some embodiments, the viral infection is an hepatitis C virus (HCV) or Human Papilloma virus (HPV). In some embodiments, the HPV (Human Papilloma Virus) is selected from HPV strains 16, 18, 31, 33, 35, 39, 45, 51, 52, 56, 58, 59, 68, 73, and 82. Each possibility is a separate embodiment. In some exemplary embodiments, the HPV strain is selected from HPV16 and HPV18 strains.

According to some embodiments, there is provided a method for treating cancer in a subject in need thereof, the method comprising administering a first composition comprising miR-122* polynucleotide molecule or a vector expressing or encoding the same and a second composition comprising one or more therapeutic reagent (drug). In some embodiments, the first and second compositions may be administered simultaneously, or sequentially, at any time interval there between.

In some embodiments, there is provided a method for treating cervical cancer in a subject in need thereof, the method comprising administering to said subject a composition comprising miR-122* polynucleotide molecule or a vector expressing or encoding the same and a reagent capable of reducing expression or activity of HPV E6 gene, HPV E7 gene or both. In some embodiments, the miR-122* molecule comprises or consists of nucleotide sequence of SEQ ID NO:1. In some embodiments, the miR-122* comprises a seed sequence having a nucleotide sequence as set forth in SEQ ID NO:2. In some embodiments, the polynucleotide molecule comprises at least one modified nucleotide. In some embodiments, the reagent capable of reducing expression or activity of E6 gene is an siRNA molecule directed against the E6 gene. In some embodiments, the reagent capable of reducing expression or activity of E7 gene is an siRNA molecule directed against the E7 gene. In some embodiments, the cervical cancer was caused by HPV infection, HCV infection, or both.

In some embodiments, there is provided a method for treating cervical cancer in a subject in need thereof, the method comprising administering to said subject a first composition comprising miR-122* polynucleotide molecule or a vector expressing or encoding the same; and a second composition comprising a reagent capable of reducing expression or activity of E6 gene and/or E7 gene. In some embodiments, the miR-122* molecule comprises or consists of nucleotide sequence of SEQ ID NO:1. In some embodiments, the miR-122* comprises a seed sequence having a nucleotide sequence as set forth in SEQ ID NO:2. In some embodiments, the polynucleotide molecule comprises at least one modified nucleotide. In some embodiments, the reagent capable of reducing expression or activity of E6 gene or E7 gene is an siRNA molecule. In some embodiments, the first and second compositions may be administered simultaneously, or sequentially, at any time interval there between.

In some embodiments, there are provided kits comprising miR-122* polynucleotide molecule or a vector expressing or encoding the same and instructions for use thereof.

Other objects, features and advantages of the present invention will become clear from the following description and drawings.

BRIEF DESCRIPTION OF THE DRAWINGS

FIG. 1A—A bar graph showing relative expression of miR-122 and miR-122* in the indicated mice (n=4) tissues (brain, n=2; heart, n=2; lung, n=3; kidney, n=3; liver, n=4)). FIG. 1B—A bar graph showing expression of miR-122 and miR-122* in the indicated human (n=4) tissues (brain, n=2; heart, n=2; lung, n=3; kidney, n=3; liver, n=4). FIG. 1C—a bar graph showing the relative expression levels of miR-122 and miR-122* in the indicated human and mouse cancer cell lines. The mouse cancer cells are of Hepatoma. The human cancer cells are of Hepatoma (HepG2 and huh7) or Breast Cancer (MCF7). Expression was normalized to RNU6 (mice) and RNU44 (human). Error bars indicate mean+SD. FIG. 1D—A graph showing the relative expression (Ct values, accumulation of a fluorescent signal) of mir-122, miR-122* and cel-39 (C. elegans miR-39) in human blood serum samples from various patients with different liver conditions. FIG. 1E—A graph showing the relative expression of mir-122 and miR-122* in samples obtained from MDR2 KO mice liver at different time points (precancerous 3 months (3 m), 9 months (9 m), tumors, or non-tumorous tissue (NT). FIG. 1F—A graph showing the correlation between expression of mir-122 and miR-122* in samples obtained from MDR2 KO four mice liver tumors (T).

FIG. 2A—Relative miR-122* expression in Huh7 cells treated with Control antagomiR (antagomiR-ctrl (antagomiR-124), miR-122 antagomiR (antagomiR-122), or mock treated, at 24 hours and 48 hours after treatment. FIG. 2B—Relative miR-122* expression in murine liver following treatment with Ctrl antagomiR (antagomiR-ctrl), miR-SUBSTITUTE SHEET (RULE 26) 122 antagomiR (antagomiR-122), or saline treatment. Error bars indicate mean+SD and values from the mock treatment were set as 100% (1); *p<0.05; **P<0.01.

FIG. 2C—Relative miR-122 expression in Huh7 cells treated with Ctrl antagomiR (antagomiR-ctrl), miR-122 antagomiR (antagomiR-122), or mock treated, at 24 hours and 48 hours after treatment. FIG. 2D—Relative miR-122 expression in murine liver following treatment with Ctrl antagomiR (antagomiR-ctrl), miR-122 antagomiR (antagomiR-122), or saline treatment. Error bars indicate mean+SD and values from the Saline treatment were set as 100% (1); *p<0.05; P<0.01; *P<0.001.

FIGS. 3A-E—Mdm2 is a target of miR122* for post transcriptional repression. FIG. 3A shows sequence alignment of 3'UTR region of Mdm2 transcript ((SEQ ID NO:3), nucleotides 1973-1994 of NM_002392.5)) and miR-122* (SEQ ID NO:24, partial sequence of SEQ ID NO:1). As shown in FIG. 3A, the two sequences are at least partially complementary, with the seed sequence (SEQ ID NO:2) of the miR-122*100% complementary to the corresponding Mdm-2 sequence. FIG. 3B (left) shows a schematic illustration of a construct comprising a fragment from the 3' UTR of mdm2 gene (Mdm2 3'UTR), having a binding sequence of miR-122* (indicated by a triangle). The construct further includes a PGK promoter sequence upstream to a Luciferase (LUC) reporter encoding sequence (LUC), and a SV40 promoter sequence (SV40), located downstream to the mdm2 3'-UTR sequence and upstream to a Renilla reporter encoding sequence. FIG. 3B (right) shows a schematic illustration of a miR-122* tester construct comprising a stretch of 4 consecutive binding (target) sites of miR-122* (4× miR-122*). The construct further includes a PGK promoter sequence upstream to a Luciferase (LUC) reporter encoding sequence (LUC) and a SV40 promoter sequence (SV40)' located downstream to the 4×-miR-122* sequence and upstream to a Renilla reporter encoding sequence. FIG. 3C—bar graphs showing results of a luciferase assay (results show relative luciferase activity normalized to Renilla activity) in HEK293 cells transfected with the mdm2-3UTR construct, or a similar construct harboring a point mutation in the miR-122* binding site within the mdm2-3'UTR (mut-3'UTR) and further transfected with either control siRNA molecules (Ctrl 1 (si-GFP), Ctrl-2 (si-SCR), miR-122* molecule (Sequences of Ctrl siRNAs and miR-122* are listed in Table 3), or empty vector (as detailed in below). FIG. 3D-bar graphs showing results of a luciferase assay (results show relative luciferase activity normalized to Renilla activity) in Huh7 cells transfected with the miR-122* tested construct or the mdm2-3'-UTR construct, and either transfected with a specific mir-122 antagomiR (antagomiR-122) or a control antagomiR (antagomiR-Ctrl). FIG. 3E—shows Western Blot analysis showing suppression of Mdm2 upon miR-122* overexpression in human cervical cancer SiHa cells (left) and HepG2 cells (right). HepG2 cells were treated with miR-122* or control miR-Scramble (si-Scr) in the presence of Pifitrin α (PFTα). The cells were treated with Nutlin-3a (a chemical inhibitor of mdm2 protein, which disrupts its interaction with p53). Cervical cancer cells, (SiHa cells), were transfected with miR-122* without PFTα treatment. Further shown is a bar graph showing quantification of the Western Blot results of the HCC (HepG2) cells. The results are normalized to Actin β(actβ) expression.

FIG. 4A—shows a schematic illustration of a p53 reporter construct comprising a stretch of 4 consecutive p53 responsive element (RE) sequences (p53REX4) from the p21 native promoter, located upstream to a reporter luciferase expression sequence. FIG. 4B—a bar graph showing the relative Luciferase/Renilla activity in siHA cells transfected with the p53REX4 construct and with either: siRNA molecule directed against E6 gene (si-E6); a control scrambled siRNA molecule (si-Scr); miR-122* molecule (miR-122*); a combination of si-E6 and miR-122* molecules; Control siRNA against luciferase (si-Luc); or no other molecule (P53RP alone). FIG. 4C—a bar graph showing the relative Luciferase/Renilla activity in HepG2 cells (harboring a wt p53), transfected with the p53REX4 construct and with either: ctrl siRNA molecule 1 (si-Scr (SEQ. ID NO: 19)), ctrl siRNA molecule 2 (miR-124 (SEQ ID NO 17)), miR-122* molecule, or no other molecule (P53RP alone). For FIGS. 4B-C, the luciferase activity was normalized by Renilla luciferase activity. Values represent mean±SD (n=3). FIG. 4D shows pictographs of luciferase expression in the liver of mice that have been injected with the p53REX4 DNA construct, by tail vain injection, along with miR-122* molecule (miR-122*) or control si-RNA molecules (si-Scr or si-Mdm2). The images were taken using IVIS (Caliper, lifeSciencse), at the indicated time points (hours after injection).

FIGS. 6A-C Activity of miR-122* leads to inhibition of cancer cells growth. FIG. 6A—siHa cells (human cervical cancer cell line) were transfected with miR-122* molecule, or mir-122 molecule or si-Scr molecule, or not treated (NT). 40 hours post transfection, the cells were visualized by phase contrast microscope and stained by crystal violet solution. The pictograms are shown in the upper panel of FIG. 6A (4× magnification). The bar graphs in the lower panel of FIG. 6A shows quantification of the results, illustrating the well density (live cells) in the transfected cells (miR-122*, mir-122 and si-Scr), or in the control, non-treated cells. Error bars indicated mean+SD. FIG. 6B—HepG2 cells (human hepatocellular carcinoma cell line) were transfected with either: miR-122* molecule, or control siRNA (si-Scr), and where indicated were further treated with PFT-α (inhibitor of p53). In addition, non treated cells (HepG2, UT) or cells non transfected but treated with PFTα, were used. The various cells were analyzed by Flow cytometry analysis (FACS) of propidium iodide (PI)-stained cells (i.e. apoptotic rate was determined). The upper panel of FIG. 6B shows the FACS analysis and the lower panel shows quantification of the results (change in percentage of PI stained cells). FIG. 6C—pictograms of HEK293 cells, non-treated or transfected with miR-122* molecule or si-Scr molecule (si-Scr), 24 hours and 48 hours after transfection. The pictograms (4× magnification, phase contrast images) show the cell density of the cells before transfection, 24 hours and 48 hours after transfection.

FIG. 7A show representative images displaying increased TUNEL signal in HepG2 cells 40 h after introduction of miR-122*, control siRNA (si-ctrl) or siRNA against Mdm2 (si-Mdm2). Scale bar, 20 μm. FIG. 7B shows line graphs demonstrating the inhibitory effect of miR-122* on tumor growth in a NOD-.SCID mouse xenograft model, as compared to the control (si-Ctrl) treatment (n=9 per group); * p<0.05. FIG. 7C shows representative images displaying increased TUNEL signal 3 days after the first intra-tumoral injection of miR-122* as compared to si-Ctrl-treated tumors. Scale bar, 1000 μm. DAPI staining of the cells is also presented. FIG. 7D shows whole-slide imaging of H&E stained tumors 3 days after the first treatment with miR-122* or with control siRNA (si-Ctrl). Large necrotic areas (black dashed line) can be observed in miR-122*-treated tumors. Scale bar, 20 μm. FIGS. 7E-F show bar graphs demonstrating the relative expression of miR-122* and Mdm2 mRNA levels, respectively, in tumors, one day after the last intra-tumoral injection of miR-122* or si-Ctrl. The relative expression was determined by qPCR and normalized to RNU6 or GAPDH, respectively.

FIG. 8B shows line graphs demonstrating the effect of miR-122* on in-vivo tumor growth (in xenograft mice model). SiHa cells were implanted subcutaneously into the flanks of NOD-.SCID mice xenograft model. The tumors generated by the SiHA cells in the xenograft mice were treated with miR-122*, si-E6 (siRNA against the viral oncoprotein E6) or control miRNA molecules (n=6 per group). The size (volume) of the tumors was determined at the indicated time points (days after injection). The results of the direct injections of miR-122* into established tumors on the tumor growth (volume) relative to the control treatments are shown in the graphs of FIG. 8B. FIG. 8C—Graphs showing one way analysis of variance (ANOVA), performed to compare the change in tumor volume within each treatment group (of FIG. 8B), 23 days after the first injection. FIGS. 8D-E— show bar graphs demonstrating the relative expression of miR-122* and Mdm2 mRNA levels, respectively, in SiHa cells-derived tumors one day after the last intra-tumoral injection of miR-122*, si-E6 or si-Scr into the tumors. The relative expression was determined by qPCR and normalized to RNU6 or GAPDH, respectively.

DETAILED DESCRIPTION OF THE INVENTION

Figure 1A:
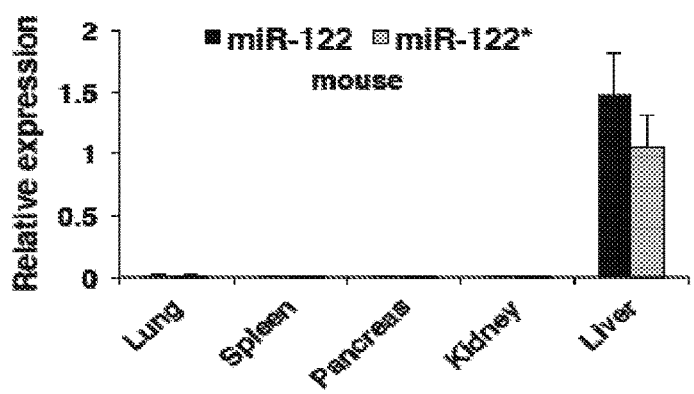
FIGS. 1A-F—Graphs showing relative expression of miR122* and miR122 in various mice and human tissues or cell lines, as determined by quantitative RT-PCR (qRT-PCR) analysis.

According to some embodiments, the present invention provides for miR-122* molecule as an active microRNA molecule, capable of specifically affecting expression or activity of target genes. Further provided are compositions comprising the miR-122* molecule or vectors encoding the same, and uses thereof for treatment of various conditions.

Definitions

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As referred to herein, the terms "polynucleotide molecules", "oligonucleotide", "polynucleotide", "nucleic acid" and "nucleotide" sequences may interchangeably be used. The terms are directed to polymers of deoxyribonucleotides (DNA), ribonucleotides (RNA), and modified forms thereof in the form of a separate fragment or as a component of a larger construct, linear or branched, single stranded (ss), double stranded (ds), triple stranded (ts), or hybrids thereof. The term also encompasses RNA/DNA hybrids. The polynucleotides may be, for example, sense and antisense oligonucleotide or polynucleotide sequences of DNA or RNA. The DNA or RNA molecules may be, for example, but are not limited to: complementary DNA (cDNA), genomic DNA, synthesized DNA, recombinant DNA, or a hybrid thereof or an RNA molecule such as, for example, mRNA, shRNA, siRNA, miRNA, and the like. Accordingly, as used herein, the terms "polynucleotide molecules", "oligonucleotide", "polynucleotide", "nucleic acid" and "nucleotide" sequences are meant to refer to both DNA and RNA molecules. The terms further include oligonucleotides composed of naturally occurring bases, sugars, and covalent inter nucleoside linkages, as well as oligonucleotides having non-naturally occurring portions, which function similarly to respective naturally occurring portions.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As referred to herein, the term "complementarity" is directed to base pairing between strands of nucleic acids. As known in the art, each strand of a nucleic acid may be complementary to another strand in that the base pairs between the strands are non-covalently connected via two or three hydrogen bonds. Two nucleotides on opposite complementary nucleic acid strands that are connected by hydrogen bonds are called a base pair. According to the Watson-Crick DNA base pairing, adenine (A) forms a base pair with thymine (T) and guanine (G) with cytosine (C). In RNA, thymine is replaced by uracil (U). The degree of complementarity between two strands of nucleic acid may vary, according to the number (or percentage) of nucleotides that form base pairs between the strands. For example, "100% complementarity" indicates that all the nucleotides in each strand form base pairs with the complement strand. For example, "95% complementarity" indicates that 95% of the nucleotides in each strand from base pair with the complement strand. The term sufficient complementarity may include any percentage of complementarity from about 30% to about 100%.

The term "construct", as used herein refers to an artificially assembled or isolated nucleic acid molecule which may be comprises of one or more nucleic acid sequences, wherein the nucleic acid sequences may be coding sequences (that is, sequence which encodes for an end product), regulatory sequences, non-coding sequences, or any combination thereof. The term construct includes, for example, vectors, plasmids but should not be seen as being limited thereto.

As used herein the term "vector" refers to constructs engineered to encode or express polynucleotides in a target cells, such as DNA, RNA, miRNA, shRNA, siRNA and antisense oligonucleotides. Vectors may include such vectors as, but not limited to, viral and non-viral vectors. The term "Expression vector" refers to vectors that have the ability to incorporate and express heterologous nucleic acid fragments (such as DNA) in a foreign cell. In other words, an expression vector comprises nucleic acid sequences/ fragments (such as DNA, mRNA, tRNA, rRNA), capable of being transcribed or expressed in a target cell. Many viral, prokaryotic and eukaryotic expression vectors are known and/or commercially available. Selection of appropriate expression vectors is within the knowledge of those having skill in the art.

The terms "promoter element", "promoter" or "promoter sequence" as used herein, refer to a nucleotide sequence that is generally located at the 5' end (that is, precedes, located upstream) of the coding sequence and functions as a switch, activating the expression of a coding sequence. If the coding sequence is activated, it is said to be transcribed. Transcription generally involves the synthesis of an RNA molecule (such as, for example, a mRNA) from a coding sequence. The promoter, therefore, serves as a transcriptional regulatory element and also provides a site for initiation of transcription of the coding sequence into mRNA. Promoters may be derived in their entirety from a native source, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions, or at various expression levels. Promoters which cause a gene to be expressed in most cell types at most times are commonly referred to as "constitutive promoters". Promoters that derive gene expression in a specific tissue are called "tissue specific promoters".

The terms "Upstream" and "Downstream", as used herein refers to a relative position in a nucleotide sequence, such as, for example, a DNA sequence or an RNA sequence. As well known, a nucleotide sequence has a 5' end and a 3' end, so called for the carbons on the sugar (deoxyribose or ribose) ring of the nucleotide backbone. Hence, relative to the position on the nucleotide sequence, the term downstream relates to the region towards the 3' end of the sequence. The term upstream relates to the region towards the 5' end of the strand.

As used herein, the terms "introducing" and "transfection" may interchangeably be used and refer to the transfer of molecules, such as, for example, nucleic acids, polynucleotide molecules, vectors, and the like into a target cell(s), and more specifically into the interior of a membrane-enclosed space of a target cell(s). The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, injection, and the like, or combinations thereof. The transfection of the cell may be performed on any type of cell, of any origin, such as, for example, human cells, animal cells, plant cells, and the like. The cells may be isolated cells, tissue cultured cells, cell lines, cells present within an organism body, and the like.

As referred to herein, the term "Treating a disease" or "treating a condition" is directed to administering a composition, which comprises at least one reagent (which may be, for example, one or more polynucleotide molecules, one or more expression vectors, one or more substance/ingredient, and the like), effective to ameliorate symptoms associated with a disease, to lessen the severity or cure the disease, or to prevent the disease from occurring. Administration may include any administration route.

The term "organism" refers to a mammal. In some embodiments, the organism is human. In some embodiments, the organism is selected from a pet, a rodent, a farm animal, and a lab animal.

The terms "subject", "patient" or "individual" generally refer to a human, although the methods of the invention are not necessarily limited to humans, and should be useful in other mammals.

As used herein, the term "E6" refers to the E6 gene or protein of the Human Papiloma Virus (HPV). The term "E7" refers to the E7 gene or protein of the Human Papiloma Virus (HPV). The oncoproteins E6 and E7 are the primary viral factors responsible for initiation and progression of cervical cancer.

As used herein the term "small interfering RNA" and "siRNA" are used interchangeably and refer to a nucleic acid molecule mediating RNA interference or gene silencing. The siRNA inhibits expression of a target gene and provides effective gene knock-down.

As used herein the terms "antisense", "antisense oligonucleotide" may interchangeably be used and refer to nucleic acids, preferably, DNA, RNA or derivatives thereof, that are complementary to the nucleotide sequences of a target RNA, characterized in that they binds to the target RNA and interfere with its activity. In some embodiments, antisense oligonucleotides also encompass antagomiR molecule, which is directed against a miRNA molecule.

The terms "microRNA" and "miRNA" are directed to a small non-coding RNA molecule that can function in transcriptional and post-transcriptional regulation of target gene expression.

As referred to herein, the terms "miR-122*", "miR-122* molecule", "mir-122*", "mir-122* molecule", "mimic-Mir-122*", "mir-122-3p" and "miR-122 passenger strand" may interchangeably be used. The terms refer to a polynucleotide molecule derived from the 3' arm of the pre-miRNA-122. The 5' arm of the pre-miRNA-122 is referred to herein as "miR-122". As detailed above, the pre-miRNA molecule is cleaved/processed to yield two RNA molecules (strands), derived from the two arms of the pre-miRNA: the "Guide strand" (5p arm) which is the strand that is usually retained in the mature RISC complex, and the "passenger strand" (3p arm), which is the strand that is discarded from the mature RISC complex. (The guide strand is often referred to as "miRNA" and the passenger strand is often referred to as "miRNA*"). In most instances, the miRNA is the more abundant strand, whereas the miRNA* strand is the less abundant strand. The seed sequence (region) of a microRNA molecule is located at positions 2-8 of the miRNA sequence, and is important in target gene recognition.

In some embodiments, the nucleotide sequence of the miR-122* comprises or consists of any one of the nucleic acids sequence of Accession numbers: MIMAT0004590, MIMAT0006826, MIMAT0017005, MIMAT0017116, MIMAT0021724, MIMAT0025429, MIMAT0026550, MIMAT0026659 and MIMAT0026987. (MirBase database).

In some embodiments, miR-122* comprises a seed sequence having a nucleotide sequence as set forth in SEQ ID NO:2. In some embodiments, the miR-122* molecule may include one or more nucleotide modifications. Each possibility is a separate embodiment.

In some exemplary embodiments, the nucleotide sequence of the miR-122* comprises or consists of the sequence: (5'-3'): AACGCCAUUAUCACACUAAAUA (SEQ ID NO: 1). It is to be understood the SEQ ID NO: 1 may include one or more nucleotide or other modifications.

In some exemplary embodiments, the nucleotide sequence of the miR-122* comprises the seed sequence: (5'-3'): ACGCCA (SEQ ID NO: 2). It is to be understood the SEQ ID NO: 2 may include one or more nucleotide or other modifications.

In some embodiments, the miR-122* may be modified at the base moiety, sugar moiety, or phosphate backbone, for example, in order to improve stability of the molecule, hybridization, transport into the cell, and the like. In addition, modifications can be made to reduce susceptibility to nuclease degradation. The miR-122* may have other appended groups such as peptides (for example, for targeting host cell receptors in vivo), or agents facilitating transport across the cell membrane or the blood-brain barrier, hybridization-triggered cleavage agents or intercalating agents. Various other well known modifications can be introduced as a means of increasing intracellular stability and half-life. Possible modifications include, but are not limited to, the addition of flanking sequences of ribo- or deoxy-nucleotides to the 5' and/or 3' ends of the molecule. In some circumstances where increased stability is desired, nucleic acids having modified internucleoside linkages such as 2'-O-methylation may be used. Nucleic acids containing modified internucleoside linkages may be synthesized using reagents and methods that are well known in the art.

In some embodiments, the miR-122* molecule may be introduced to a cell, a tissue or an organism by any of the methods known in the art. In some embodiments, the miR-122* molecule may be introduced in the form of a composition. In some embodiments the composition is a pharmaceutical composition, comprising one or more suitable excipients. In some embodiments, the miR-122* may be expressed or encoded in a target cell, tissue or organism be an exogenous vector introduced thereto. In some embodiments the vector may be comprised in a composition. In some embodiments, the vector may be introduced to a cell, tissue or organism by any of the methods known in the art. In some exemplary embodiments, the miR-122* may be introduced in the form of a single strand RNA molecule (ssRNA), double strand RNA molecule (dsRNA), or an RNA molecule which is at least partially double stranded. Each possibility is a separate embodiment.

In some embodiments, the miR-122* may be introduced or expressed or encoded in a cell, tissue or organism in combination with one or more additional reagent. In some embodiments, the additional reagent may be a therapeutic reagent (drug). In some embodiments, the additional reagents may include other polynucleotide molecule(s). In some embodiments, the miR-122* (or a vector encoding or expressing the same) and the additional reagent may be administered in the same or different composition and they may be administered simultaneously, or sequentially, at any time interval.

In some embodiments there is provided a composition comprising a miR-122* polynucleotide or a vector encoding or expressing said miR-122* polynucleotide.

According to some embodiments, a target gene of miR-122* comprises a sequence that is at least partially complementary to the nucleotide sequence of the miR-122*. In some embodiments, the target gene of miR-122* comprises a sequence that is 100% complementary to the sequence of the mir-122*. In some embodiments, the target gene of miR-122* comprises a sequence that is at least 95% complementary to the sequence of the mir-122*. In some embodiments, the target gene of miR-122* comprises a sequence that is at least 90% complementary to the sequence of the mir-122*. In some embodiments, the target gene of miR-122* comprises a sequence that is at least 85% complementary to the sequence of the mir-122*. In some embodiments, the target gene of miR-122* comprises a sequence that is at least 80% complementary to the sequence of the mir-122*. In some embodiments, the target gene of miR-122* comprises a sequence that is at least 70% complementary to the sequence of the mir-122*. In some embodiments, the target gene of miR-122* comprises a sequence that is at least 60% complementary to the sequence of the mir-122*. In some embodiments, the target gene of miR-122* comprises a sequence that is at least 50% complementary to the sequence of the mir-122*. In some embodiments, the target gene of miR-122* comprises a sequence that is at least partially complementary to the seed sequence of miR-122* molecule. In some embodiments, the target gene of miR-122* comprises a sequence that is at 100% complementary to the seed sequence of miR-122* molecule.

According to some embodiments, miR-122* is a functional micro-RNA (miRNA), capable of affecting expression of various target genes, at least some of which are involved in the regulation of the cell cycle, such as Mdm2.

In some exemplary embodiments, a target gene of miR-122* is Mdm2 (Mouse double minute 2 homolog, also known as E3 ubiquitin-protein ligase Mdm2, (exemplary accession numbers: NM_002392.5; NM_001288586.1)), which is a negative regulator of the p53 tumor suppressor gene. The Mdm2 protein functions both as an E3 ubiquitin ligase that recognizes the N-terminal trans-activation domain (TAD) of the p53 tumor suppressor and as an inhibitor of p53 transcriptional activation. As exemplified herein below, the 3'-UTR region of the Mdm-2 transcript contains a nucleotide sequence that is at least partially complementary to the Mir-122* sequence, and is 100% complementary to the seed sequence of the Mir-122*. As further exemplified herein below, miR-122* is capable of reducing the expression level of the mRNA and/or protein of Mdm2 in target cells.

In some embodiments, a target gene of miR-122* is WRAP53. In some embodiments, the accession number of WRAP53 is selected from: NM_001288586.1, NM_001143990.1, NM_001143991.1, NM_018081.2, and NM_001143992.

According to some embodiments, there is provided a method for reducing expression of Mdm2 in a target cell, the method comprising introducing into the target cell a miR-122* polynucleotide molecule, thereby reducing expression of MDM2 in the target cell. In some embodiments, the method comprises introducing into the cell a vector encoding for or expressing the miR-122* polynucleotide molecule in the target cell. In some embodiments, expression of the Mdm2 is expression of the Mdm2 mRNA, Mdm2 protein or both. In some embodiments the miR-122* or the vector expressing or encoding the same may be introduced in the form of a formulation. In some embodiments, there is provided the use of a miR-122* polynucleotide molecule or a vector expressing or encoding the same for reducing expression of Mdm2 in a target cell. In some embodiments, there is provided a composition comprising miR-122* polynucleotide molecule or a vector expressing or encoding the same for reducing expression of Mdm2 in a target cell. In some embodiments, the composition is a pharmaceutical composition that may further include one or more suitable excipients.

According to some embodiments, there is provided a method of enhancing p53 expression, stability or activity, in a target cell, the method comprising introducing into the target cell a miR-122* polynucleotide molecule or a vector encoding for or expressing the miR-122* in the target cell, thereby enhancing p53 expression, stability or activity. The cell may be harbored in a tissue or organism.

According to some embodiments, there is provided the use of a miR-122* polynucleotide molecule or a vector expressing or encoding the same for enhancing p53 expression, stability or activity in a target cell.

In some embodiments there is provided a method of treating a condition associated with p53, the method comprising administering a composition comprising miR-122* polynucleotide molecule or a vector expressing or encoding the same to a subject in need thereof.

In some embodiments, there is provided a composition comprising miR-122* polynucleotide molecule or a vector expressing or encoding the same for enhancing expression and/or activity and/or stability of p53 in a target cell. In some embodiments, the composition is a pharmaceutical composition that may further include one or more suitable excipients.

According to some embodiments, there is provided a method for inducing cell death of a cancer cell, the method comprising introducing into the cancer cell a miR-122* polynucleotide molecule or a vector expressing or encoding the same. In some embodiments, the cancer cell is harbored in a tissue or organism. In some embodiments, the cancer cell is any type of cancer cell. In some exemplary embodiments, the cancer cell is of hepatic origin or cervical origin.

In some embodiments, there is provided the use of a miR-122* polynucleotide molecule or a vector expressing or encoding the same for inducing cancer cell death.

In some embodiments, there is provided a composition comprising miR-122* polynucleotide molecule or a vector expressing or encoding the same for inducing cancer cell death. In some embodiments, the composition is a pharmaceutical composition that may further include one or more suitable excipients.

According to some embodiments, there is provided a method for inhibiting or reducing growth of cancer cells, the method comprising introducing into the cell a miR-122* polynucleotide molecule or a vector expressing or encoding the same. In some embodiments, the miR-122* molecule comprises or consists of nucleotide sequence of SEQ ID NO: 1. In some embodiments, the miR-122* comprises a seed sequence having a nucleotide sequence as set forth in SEQ ID NO:2. In some embodiments, the polynucleotide molecule comprises at least one modified nucleotide. In some embodiments, the cell is harbored in a tissue or organism. In some embodiments, the cancer cell is of hepatic origin or cervical origin. In some embodiments, reducing growth comprises reducing growth rate.

In some embodiments there is provided the use of miR-122* polynucleotide molecule or a vector expressing or encoding the same for inhibiting or reducing growth of cancer cells.

In some embodiments, there is provided a composition comprising miR-122* polynucleotide molecule or a vector expressing or encoding the same for inhibiting or reducing cancer cell growth. In some embodiments, the composition is a pharmaceutical composition that may further include one or more suitable excipients.

According to some embodiments, there is provided a method for treating cancer in a subject in need thereof, the method comprising administering a composition comprising miR-122* polynucleotide molecule or a vector expressing or encoding the same. In some embodiments, the miR-122* molecule comprises or consists of nucleotide sequence of SEQ ID NO:1. In some embodiments, the miR-122* molecule comprises a nucleotide sequence of SEQ ID NO:2. In some embodiments, the polynucleotide molecule comprises at least one modified nucleotide. In some embodiments, the cancer originated from a viral infection. In some embodiments, the viral infection is an HCV or HPV.

In another embodiment, cancer is adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, small cell, lymphoma, AIDS-related, lymphoma, central nervous system (primary), lymphoma, cutaneous T-cell, lymphoma, hodgkin's disease, non-hodgkin's disease, malignant mesothelioma, melanoma, merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, sezary syndrome, skin cancer, cutaneous T-cell lymphoma, skin cancer, kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, or wilms' tumor.

In some embodiments, cancer is a non-solid tumor such as a blood cancer. In another embodiment, a non-solid tumor or blood cancer is leukemia or lymphoma. In another embodiment, a non-solid tumor or blood cancer is acute lymphoblastic leukemia (ALL). In another embodiment, a non-solid tumor or blood cancer is acute myelogenous leukemia (AML). In another embodiment, a non-solid tumor or blood cancer is chronic lymphocytic leukemia (CLL). In another embodiment, a non-solid tumor or blood cancer is small lymphocytic lymphoma (SLL). In another embodiment, a non-solid tumor or blood cancer is chronic myelogenous leukemia (CML). In another embodiment, a non-solid tumor or blood cancer is acute monocytic leukemia (AMOL). In another embodiment, a non-solid tumor or blood cancer is Hodgkin's lymphomas (any of the four subtypes). In another embodiment, a non-solid tumor or blood cancer is Non-Hodgkin's lymphomas (any of the subtypes). In another embodiment, a non-solid tumor or blood cancer is myeloid leukemia.

In some embodiments, cancers include such cancers as: carcinomas, sarcomas, myelomas, leukemias, lymphomas and mixed type tumors. Particular categories of tumors include lymphoproliferative disorders, breast cancer, ovarian cancer, prostate cancer, cervical cancer, endometrial cancer, bone cancer, liver cancer, stomach cancer, colon cancer, lung cancer, pancreatic cancer, cancer of the thyroid, head and neck cancer, cancer of the central nervous system, cancer of the peripheral nervous system, skin cancer, kidney cancer, as well as metastases of all the above. Particular types of tumors amenable to treatment include: hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to certain embodiments, the cancer is selected from cervical cancer, hepatic cancer, prostate cancer, breast cancer, skin cancer, colon cancer, lung cancer, pancreatic cancer, lymphoma, myeloma, leukemia, head and neck cancer, kidney cancer, ovarian cancer, bone cancer, liver cancer or thyroid cancer.

In some embodiments, the cancer comprises wild-type p53. In some embodiments, the cancer cells harbor or comprise a wild-type p53.

In some embodiments, there is provided a method for treating cervical cancer in a subject in need thereof, the method comprising administering to said subject a composition comprising miR-122* polynucleotide molecule or a vector expressing or encoding the same and a reagent capable of reducing expression or activity of the E6 gene and/or the E7 gene of HPV. In some embodiments, the miR-122* molecule comprises or consists of nucleotide sequence of SEQ ID NO:1. In some embodiments, the miR-122* comprises a seed sequence having a nucleotide sequence as set forth in SEQ ID NO:2. In some embodiments, the polynucleotide molecule comprises at least one modified nucleotide. In some embodiments, the reagent capable of reducing expression or activity of E6 gene is an siRNA molecule against the E6 gene. In some embodiments, the reagent capable of reducing expression or activity of E7 gene is an siRNA molecule against the E7 gene.

In some embodiments, there is provided a method for treating cervical cancer in a subject in need thereof, the method comprising administering to said subject a first composition comprising miR-122* polynucleotide molecule or a vector expressing or encoding the same; and a second composition comprising a reagent capable of reducing expression or activity of E6 gene and/or E7 gene. In some embodiments, the miR-122* molecule comprises or consists of nucleotide sequence of SEQ ID NO: 1. In some embodiments, the miR-122* comprises a seed sequence having a nucleotide sequence as set forth in SEQ ID NO:2. In some embodiments, the polynucleotide molecule comprises at least one modified nucleotide. In some embodiments, the reagent capable of reducing expression or activity of E6 gene or E7 gene is an siRNA molecule. In some embodiments, the first and second compositions may be administered simultaneously, or sequentially, at any time interval there between.

In some embodiments, the cervical cancer is caused by viral infection. In some embodiments, the viral infection is caused by a Human Papiloma Virus (HPV). In some embodiments, the HPV strain is any HPV strain. In some embodiments, the HPV strain is selected from HPV-16 and HPV-18.

In some embodiments, and without wishing to be bound to any theory or mechanism, targeting of E6 or E7 genes of the HPV results in accumulation of P53 in the cells, which in turn is degraded by the Mdm-2. The combined activity of the miR-122* in the target cells, as a negative regulator of Mdm-2, induces a specific cell death, of HPV-positive cervical cancer cells treated with the anti E6 or E7 agents. Thus, the combined effect of the anti-E6 and/or E7 agents with miR-122* provides a long term effect capable of inducing specific cancer cells death and consequently, treatment of the cancer condition.

According to some embodiments, various delivery systems are known and can be used to transfer/introduce the polynucleotides and/or composition of the invention into cells, such as, for example, encapsulation in liposomes, microparticles, microcapsules, electroporation, nucleofection, ultrasound based, laser based, recombinant cells that are capable of expressing the composition, receptor-mediated endocytosis, construction of the composition of the invention as part of a viral vector or other vector, viral vectors that are capable of being reproduced without killing the cell during the process of reproduction and that comprise the composition of the invention, viral vectors that are not capable of reproduction and that comprise the composition of the invention, injection of cells that produce viral vectors that comprise the composition of the invention, injection of polynucleotides, electroporation, calcium phosphate mediated transfection, and the like, or any other methods known in the art or to be developed in the future.

In some embodiments, the polynucleotide and compositions of the invention may be suitably formulated for intravenous, intramuscular, subcutaneous, intracervical, intratumoral, or intraperitoneal administration.

In some embodiments, the polynucleotide and compositions of the invention may be suitably formulated to be disposed or contained in a device, such as a contraceptive device. In such embodiments, the composition may be an immediate release or slow release composition.

In some embodiments, the polynucleotide and compositions described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

In some embodiments, where the target cells are in vivo, the polynucleotides and composition of the invention can be administered by any convenient protocol. In some embodiments, the protocol employed is a nucleic acid administration protocol, where a number of different such protocols are known in the art. For example, the nucleic acids may be introduced into tissues or host cells by any number of routes, including viral infection, microinjection, fusion of vesicles, or Jet injection for intramuscular administration. In some embodiments, the nucleic acids may be coated onto gold microparticles, and delivered intradermally by a particle bombardment device. In some embodiments, expression vectors may be used to introduce the nucleic acids into a cell. In some embodiments, the polynucleotides or compositions of the invention may be fed directly to, injected into, the host organism containing a desired target gene. In some embodiments, the polynucleotides or compositions of the invention may be directly introduced into the cell (i.e., intracellularly); or introduced extracellularly into a cavity, interstitial space, into the circulation of an organism, introduced orally, and the like. Methods for oral introduction include direct mixing of a polynucleotide (such as, RNA) with food of the organism. Physical methods of introducing polynucleotides include injection directly into the cell or extracellular injection into the organism of a polynucleotide solution (composition), such as, an RNA solution. The polynucleotides of the invention may be introduced in an amount which allows delivery of at least one copy per cell. Higher doses (for example, at least 5, 10, 100, 500 or 1000 copies per cell) of the polynucleotide may yield an enhanced effect, whereas lower doses may be useful for specific applications. In some embodiments, a hydrodynamic nucleic acid administration protocol may be used. In some embodiments, the polynucleotides of the invention can be incorporated into a variety of formulations (compositions) for therapeutic administration. More particularly, the polynucleotides of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, intratumoral, intracervical, intra-tissue and the like, administration. In pharmaceutical dosage forms, the polynucleotides may be administered alone or in appropriate association, as well as in combination, with other pharmaceutically active compounds. In some embodiments, the pharmaceutical dosage forms, may be administered locally, by being disposed or contained in a device, such as a contraceptive device, including, but not limited to intrauterine devices (such as hormonal or non-hormonal devices).

In some embodiments, the miR-122* (alone or in combination with other agents) may be administered in a dose having an amount of between about 0.01 mg and about 10 mg per administration/treatment per day. For example, when the miR-122* (alone or in combination with other agents) is administered by local injection or contained in a device, generally an amount of between about 0.01 mg and about 8 mg per administration/treatment is administered. In some embodiments, the amount is between about 0.01 mg and about 2 mg per administration/treatment. In some embodiments, the amount is between about 0.05 mg and about 4 mg per administration/treatment. In some embodiments, the amount is between about 0.05 mg and about 2 mg per administration/treatment. In some embodiments, the amount is between about 0.08 mg and about 2 mg per administration/treatment. In some embodiments, the amount is between about 0.08 mg and about 1 mg per administration/treatment. In some embodiments, the amount is between about 0.5 mg and about 9 mg per administration/treatment per day of nucleotides is administered. In some exemplary embodiments, the miR-122* (alone or in combination with other agents, such as, for example, siRNA against E6) is formulated in a saline solution (such as PBS). In some embodiments, the doses disclosed herein may be administered at any administration regime, such as, 1-5 times a day; 1-10 times a week, 1-15 times a month, and the like, at identical or different time intervals and/or at the same or different time of day.

In some embodiments, for oral preparations, the polynucleotides can be used alone or in combination with appropriate additives to make tablets, powders, granules or capsules, for example, with conventional additives, such as lactose, mannitol, polyglutamic acid (PLGA) poly lysine acid (PLA), corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In some embodiments, the polynucleotides can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, the polynucleotides can be utilized in aerosol formulation to be administered via inhalation. The compounds of the present invention can be formulated into pressurized acceptable propellants such as dichlorodifluoromethane, propane, nitrogen and the like.

In some embodiments, the polynucleotides can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

In some embodiments, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the polynucleotides in a composition as a solution in sterile water, normal saline or another pharmaceutically acceptable carrier.

In some embodiments, the pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public. Those of skill in the art will readily appreciate that dose levels can vary as a function of the specific compound, the nature of the delivery vehicle, and the like. Preferred dosages for a given compound are readily determinable by those of skill in the art by a variety of means.

In some embodiments, the compositions of the invention may be advantageously combined and/or used in combination and/or alternation with other agents which are either therapeutic or prophylactic agents, and different from the subject compounds. The compositions may also be advantageously combined and/or used in combination with agents that treat conditions often associated with the treated condition. In certain embodiments, administration in conjunction with the subject compositions enhances the efficacy of such agents.

According to some embodiments, reagents and kits thereof for practicing one or more of the above-described methods are provided. The subject reagents and kits thereof may vary greatly. Typically, the kits at least include a miR-122* molecule or a vector encoding or expressing the same, as described above. The kits may also include a pharmaceutically acceptable delivery vehicle, which may be combined with or separate from the miR-122* in the kit. In addition to those components, the kits further include instructions for practicing the subject methods.

According to yet another aspect of the invention, there is provided a kit comprising the pharmaceutical composition, essentially as described above, and instructions for use of the kit.

The terms "comprises", "comprising", "includes", "including", "having" and their conjugates mean "including but not limited to". The terms "comprises" and "comprising" are limited in some embodiments to "consists" and "consisting", respectively. The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "about" in reference to a numerical value stated herein is to be understood as the stated value +/−10%.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The following examples are presented in order to more fully illustrate some embodiments of the invention. They should, in no way be construed, however, as limiting the broad scope of the invention.

EXAMPLES

Materials and Methods
Cell Culture

Culture cells (listed in Table 1) were maintained in DMEM medium supplemented with 10% inactivated FBS, in 10 cm² plates in 5% humidified $CO_2$ at 37° C. Twice a week, cells were passaged and seeded at a concentration of $0.5×10^6$ cells/10 ml medium in 10 cm² plates. Detaching was done by incubation with 1 ml Trypsin for 2-3 min. To stop the enzymatic process, double volume of the medium was added; cells were centrifuged (400 g, 5 min, RT) and resuspended in 1 ml of fresh medium. Cells were counted in a haematocytometer under light microscope (magnification ×10) immediately after the addition of Trypan blue solution (1:10 ratio). Non-stained cells were considered viable. The percentage of viable cells was determined in relation to total cells. For the experiments, the cells were seeded $0.5×10^6$ in a 24-well plate or $0.3×10^6$ in a 6-well plate in the appropriate enriched medium and left overnight to allow adherence. Cells were transfected as described in transfection procedures, after medium was changed.

TABLE 1

| Name | Cell Type | P53 status | miR-122 Expression | miR-122* Expression |
|---|---|---|---|---|
| Huh7 | Human hepatoma cells | Mutated | High | High |
| HepG2 | Human hepatoma cells | Wild type | Low | Low |
| SiHa | Human cervical cancer | Wild type | Very low | Very low |
| Hek293 | Human embryonic kidney | Wild type | — | — |

Construction of Luciferase-Mdm2-3'UTR and Luciferase-miRNA Target Site Fusion Plasmids To construct reporter plasmids bearing miR-122* target sites, a fragment from the 3'UTR of mdm2 gene (nucleotides 1973-1994 of NM_002392.5), containing a putative miR-122* was synthesized by PCR amplification using a set of primers P611 and P612 (Table 2) and cDNA prepared (as described below) from HepG2 (human) cells RNA extract. Reaction conditions were: 94° C. for 5 min, followed by 30 cycles of 90° C. for 30 sec; 58° C. for 30 sec; 72° C. for 30 sec. The PCR product analyzed on 2% Agarose gel and the fragment of 240 bp was extracted using the Promega kit. The isolated PCR fragment (mdm2-3'UTR) and the pmiRGLO vector were digested with SacI and XbaI restriction enzymes at 37° C. Over night (O.N.). The digestion products were analyzed on 2% agarose gel and the 7325 bp fragment of pmiRGLO vector was isolated from the agarose gel using the Promega kit.

To construct reporter vector bearing 2 synthetic miR-122* target sites, the antisense and sense strands of the oligonucleotides P607 and P608 (containing 2 synthetic recognition sequences of miR-122*, Table 2)) were annealed by adding 2 µg of each oligonucleotides to 46 µl of annealing solution and incubated at 90° C. for 5 min and then at 37° C. for 1 h. Annealing of these oligonucleotides produces 3'-overhang (allowing ligation into the SacI and XbaI sites in the pmiRGLO vector) at their 3' and 5' ends.

The above described inserts (mdm2-3'UTR or miR-122* target sites) were ligated into SacI and XbaI sites in the pmiRGLO vector at 4° C. O.N. (T4 DNA ligase) and transformed into DH5α competent cells by heat shock.

To construct reporter plasmid containing 4 synthetic miR-122* ("miR-122* tester") target sites, an additional set of oligonucleotides, P609 and P610 (containing 2 synthetic seed sequences of miR-122* (each having the sequence, TGGCGT (SEQ ID NO:4, complementary to SEQ ID NO:2, which is the seed sequence of the miR-122* (SEQ ID NO:1) was annealed as previously described. Annealing of these oligonucleotides produces 3' and 5'-overhang (allowing ligation into the XbaI and SbfI sites in the pmiRGLO vector) at their 3' and 5' ends. The annealed oligonucleotides were ligated into the XbaI-SbfI site of pmiRGLO-miR-122* tester_1 (with 2 seed sequences of miR-122*).

TABLE 2

| Primer Name | Sequence | Derived from Gene |
|---|---|---|
| P21 | ACCACAGTCCATGCCATCAC (SEQ ID NO: 5) | GAPDH |
| P22 | TCCACCACCCTGTTGCTGTA (SEQ ID NO: 6) | GAPDH |
| P219 | CCTCATAAAGGCCAAGAAGG G (SEQ ID NO: 7) | luciferase |
| P607 Antisense | CTAGAAACGCCATTATCACA CTAAATCGAACGCCATTATC ACACTAAGAGCT (SEQ ID NO: 8) | miR-122* |
| P608 Sense | CTTAGTGTGATAATGGCGTT CGATTTAGTGTGATAATGGC GTTT (SEQ ID NO: 9) | miR-122* |
| P609 Sense | CTAGATTAGTGTGATAATGG CGTTCGATTTAGTGTGATAA TGGCGTTTCCTGCA (SEQ ID NO: 10) | miR-122* |
| P610 Antisense | GGAACGCCATTATCACACTA AATCGAACGCCATTATCACA CTAAT (SEQ ID NO: 11) | miR-122* |
| P611 Sense | ACCTCTGAGCTCATCCTTTA CACCAACTCC (SEQ ID NO: 12) | Mdm2 |
| P612 Antisense | GATGACTCTAGACCAAGCTA ATTGGGAGGC (SEQ ID NO: 13) | Mdm2 |

Transformation and Colony Analysis

Each ligation product was added into 150 µl of DH5α competent cells and incubated for 30 min on ice. Then, the cells were transferred into 42° C. bath for 2 min followed by 5 min incubation on ice. The recovery was done by adding 500 µl of LB into each transformation and incubation at 37° C. for 1 h. After the incubation, the transformed cells were centrifuged at 3800 g for 2 min, the supernatant was discarded and the pellets were resuspended in 100 µl LB for seedling on LB-Amp plates. On the next day, colony direct PCR was performed for insert recognition using DreamTaq (Fermentas). The primers used were as follows: for mdm2-3'UTR insert detection, P611 and P219; and for miR-122* seed sequences detection, P608 and P219. PCR conditions: 94° C. for 3 min, 30 cycles of PCR at 94° C. for 30 sec, 56° C. for 30 sec and 72° C. for 30 sec, 72° C. for 15 min and 4° C. for 15 min Individual colonies were grown in 12 ml LB containing Ampicillin for the analysis. The integrity and the orientation of the construct were confirmed by restriction endonuclease analysis and DNA sequencing.

Transfection Procedures

For luciferase assays, cells in 24 well plates were transfected using the manufacturer protocol of Lipofectamine 2000 transfection reagent, as follows:

p53-responsive plasmid (P53 RP) (90 ng) was co-transfected with 1 ng *Renilla reniformis* plasmid (pEF-RL) and mimic-miR-122* (30 nM) or mimic-microRNA control (Table 3) into HepG2 cells;

PmiRGLO-containing four miR-122* synthetic sites (80 ng) or pmiRGLO-containing the mdm2-3'UTR (80 ng) together with miR-122* molecule (30 nM) or control microRNA (miR-124) were co-transfected into Hek293 cells. Each transfection received the same amount of total DNA.

For RNA analysis and cell viability assays, Huh7, HepG2 and SiHa cells were transfected using the manufacturer protocol of Lipofectamine 2000 transfection reagent. AntagomiR-122 (30 nM) and antagomiR-124 (30 nM) were transfected into 6-well plates for 24 hrs and 48 hrs. miR-122*, miR-122, si-E6 or si-Scr (scrambled sequence) were transfected into 6-well plates at various concentrations (30 nM-150 nM).

For all experiments, the transfection performed using serum-free medium (OPTIMEM).

For Western Blot and/or flow cytometry assays HepG2 cells were treated with 10 µM of PFTα (Sigma Aldrich; P4359), an inhibitor of p53 and/or with 20 µM of Nutlin-3a (Sigma Aldrich; SML0580) to abolish the activity of endogenous mdm2.

TABLE 3

| Name | Type | Sequence |
|---|---|---|
| antagomiR-122 | Antisense | 5'-AsCsACACAACACUGUCACA UUsCsCsAs-Chol-3' (SEQ ID NO: 14) |
| antagomiR-18a | Antisense | 5-CsUsAUCUGCACUAGAUGCAC CsUsUsAs-Chol-3' (SEQ ID NO: 15) |
| antagomiR-124 | Antisense | 5'-GsGsCAUUCACCGCGUGCsC sUsUs-Chol-3' (SEQ ID NO: 16) |
| miR-122* | Mimicate | 5'-AACGCCAUUAUCACACUAAA UA-Biotin-3' (SEQ ID NO: 23) |
| miR-124 | Mimicate | 5'-UAAGGCACGCGGUGAAUGC C-3' (SEQ ID NO: 17) |
| si-GFP | siRNA | 5'-GCUGACCCUGAAGUUCAU C-3' (SEQ ID NO: 18) |
| si-Scr | siRNA | 5'-CACCACAUACCGCACGG-Biotin-3' (SEQ ID NO: 19) |
| si-E6 | siRNA | 5'-UCCAUAUGCUGUAUGUGA U-3' (SEQ ID NO: 20) |
| si-luc | siRNA | 5'-CUUACGCUGAGUACUUCG A-3' (SEQ ID NO: 21) |
| si-mdm2 | siRNA | 5'-AGGCUUGGAUGUGCCUGAU GGCAAA-3' (SEQ ID NO: 22) |

Chemical Modifications of the antagomiR Oligos (SEQ ID NOs 14-16) Listed in Table 3:

The upper case letters represent 2'-O Me-modified nucleotides; Subscript 's' represents a phosphorothioate linkage; 'Choi' represents cholesterol linked through a hydroxyprolinol linkage. The miR-122* and si-Scr oligonucleotides are modified with biotin molecule at the 3' end.

Luciferase Activity Assay

Following transfection for 48 hrs, the cells were lysed with a lysis buffer provided in the kit (shaking for 20 min at RT) and transferred into Nunc 96-well plate. Luciferase activities were measured by Dual-Luciferase Assay System (Promega) on a luminometer (Mithras 2000).

RNA Isolation

Total RNA from various cell lines and mice tissues was isolated using Trizol reagent (Invitrogen), followed by DNaseI treatment using the DNaseI Kit (Ambion).

Cells: The cells were lysed by adding 1 ml Trizol reagent directly into the well and incubated for 5 minutes at RT.

Tissues: 1 ml Trizol was added to ~100 mg of murine tissue and homogenized using the homogenizer (PolyTron Kinematica, Luzern, Switzerland). After the homogenization, the lysate was incubated for 5 min at RT.

Cells and tissues: 200 µl chloroform were added to the Trizol-containing lysates, mixed by vortexing for 20 sec and incubated for 3 min at RT. Then, the samples were centrifuged for 15 min at max speed at 4° C. The upper aqueous phase was transferred into fresh tube and the RNA was precipitated in 100% Ethanol at −20° C. for O.N. Next day, the samples were centrifuged for 40 min at max speed at 4° C. The pellets were washed (×2) with 85% Ethanol. Then, the pellets were briefly vacuum-dried and redissolved in 50 µl DDW-DEPC for 10 min at 65° C. The concentrations were measured by Nanodrop (ND spectrophotometer, Wilmington, Del., USA) and the integrity was analyzed by gel electrophoreses on a 1% agarose gel.

Quantitative Real-Time RT-PCR Analysis mRNA levels were measured using Reverse Transcription (RT) Real-Time PCR. For cDNA preparation, 1.5 µg of total RNA extracted from each liver was incubated with 1 µg of Random Primers and 5 units of RNAsine inhibitor for 5 min at 95° C. After gradual reduction of the temperature to 42° C., a mix containing the Moloney murine leukemia virus Reverse transcriptase enzyme (MMLV RT) and 12 µM of dNTPs was added to each sample and incubated for 1 h at 42° C. To ensure that the cDNA does not contain any residual DNA templates, an additional cDNA reaction was performed without the MMLV Reverse transcriptase enzyme. The products were analysed by PCR reaction using primers specific for GAPDH gene capable of DNA detection. These cDNAs provided a template for Real-Time PCR reaction with specific Taqman probe and primers set. The real time PCR reaction for the detection of H19, AldoA, mdm2 and GAPDH was performed according to the manufacturer instructions using ABI 7900HT fast Real-Time PCR system. The cDNA for microRNAs detection was prepared using Taqman microRNA reverse transcription kit which includes the pre-amplification step with a specific primer for each microRNA. The levels of miR-122, miR-122*, miR-18a and RNU43 were then measured by real time PCR using the Taqman probe and primers set. The cDNA and the Real-Time PCR reaction were carried out on the ABI 7900HT fast Real-Time PCR system. Threshold cycle numbers (Ct) were determined with Sequence Detector Software (version 1.6; Applied Biosystems) and transformed using the ΔCt method as described by the manufacturer.

Bradford Protein Quantification Assay

The protein content of each lysate sample was quantified by Bradford assay. A standard curve of OD against increasing protein concentration was established for each protein sample using serial dilutions of BSA standard protein (1 mg/ml) and a Coomassie blue based dye reagent. Sample protein concentrations were calculated from a standard curve made with standard protein. 3 µl unknown samples were incubated with 1 ml of Coomassie reagent (diluted 1:5 with DDW) and OD at 595 nm immediately was measured by spectrophotometer.

Western Blot Analysis

Lysates were obtained from the mice liver tissue. Cells were lysed by the addition of 1 ml protein lysis buffer. Protein amounts were determined by Bradford assay. Protein samples were heated (90° C., 5 min) with β-Mercaptoethanol and SDS-containing protein sample buffer. Samples were loaded on 10% polyacrylamide gel SDS-PAGE under reducing conditions. Proteins were electro-transferred from 2-D gel to PVDF membrane and were shaken for 1 h at RT with blocking solution and then washed in washing solution. Incubation with primary specific antibody ($1/10,000$) (anti-p53 Ab: DO1 sc-126; anti-mdm2 Ab: clone 2A10 hybridoma) was performed for O.N. at 4° C. After the washing procedure (3 times, 10 minutes each in washing solution), the membrane was incubated with a secondary immunopure HRP-conjugated antibody ($1/10000$), washed (5 times, 6 min) and detected with the ECL kit. Photon emission was identified by the exposure to photography film development. Intensities of protein bands were quantified by computerized densitometry using Image Gauge software.

Cell Viability and Flow Cytometry

HepG2 (human HCC) or SiHa (human cervical cancer) cells were transfected with miR-122* or siScr. The cells were simultaneously fixed (20% methanol) and stained with crystal violet solution at different time point post-transfection. Well densities were analyzed using the Image Lab software (BioRad). The apoptotic rate was detected by AnnexinV-PI double staining according to manufacturer protocol (Mebcyto kit, MBL international). TUNEL assay was performed according to the manufacturer's protocol (Roche Diagnostics, IN, USA). Fluorescent images were viewed by Olympus BX61 microscope (Olympus, Tokyo, Japan).

Animals

Six-week old male C57Bl/6, NOD.SCID and NUDE mice were purchased from Harlan, Israel. All mice were kept in a specific pathogen-free facility. Mice were handled according to the criteria outlined in the "Guide for the Care and Use of Laboratory Animals" prepared by the National Academy of Sciences and published by the National Institutes of Health. All animal experimentations were performed following a relevant ethical review board approval of the specific experiments.

Mice Injections and Imaging

C57Bl/6 mice were tail vein injected with 1.5 ml saline or with saline containing 5 µg of antagomiR-122 or antagomiR-18a. 48 hrs later the mice were sacrificed and the livers were frozen in liquid nitrogen for further RNA and proteins analysis.

To test the activity of P53 in vivo, P53 Responsive plasmid (P53 RP) along with miR-122*, si-Mdm2 or si-Scr were tail vein injected into 6-weeks old male Balb/c mice. 24 h, 48 h and 72 h post injection, the mice were anesthetized with a mixture of ketamine hydrochloride (150 mg/kg), xylazine (12 mg/kg). D-luciferin (50 mg/ml) was injected as a substrate for the live imaging of luciferase enzyme activity utilizing the In Vivo Imaging System (IVIS) for a duration of 60-120 s. Mice were allowed to recover under isothermic conditions after imaging. To quantify bioluminescence, identical standardized circular regions of interest (ROI) were positioned to encircle the areas of emission, and the integrated flux of photons through each ROI (photons/s) was determined using the Living Images software package.

Tumorigenicity Assays in Nude Mice

In a nude mouse model, subcutaneous tumors were generated by injection of $1.5 \times 10^6$ HepG2 cells into the right flank of male BALB/c athymic nude mice. The first Intratumoral injection of miR-122* or siScr was performed after the tumors were formed (Day 0). Tumor width (W) and length (L) were measured with caliper and tumor volume (V) was calculated with the formula $W^{2*}$ (L*0.5).

In a NOD.SCID model, subcutaneous tumors were generated by injection of either $1.5 \times 10^6$ HepG2 cells or $6 \times 10^6$ SiHa cells into the right flank of female NOD.SCID (NOD.CB17-Prkdsscid/NCrHsd) mice, using a 27-g needle.

For the HepG2-derived tumors, the first Intra-tumoral injection (10 μg/tumor) of either mimic-miR-122* or mimic-miR-Ctrl was performed after the tumors were formed (Day 0). Intra-tumoral injections of miR-122* or si-Ctrl (si-Scr) were performed every second day. Luciferase expression is proportional to the tumor size. Three days and fourteen days after the treatment, animals were euthanized and their s.c. lesions were resected and either immediately snap frozen in liquid nitrogen for RNA and protein extraction or fixed with 4% paraformaldehyde for histological examination. Images of whole tumors were taken by Nikon Eclipse Ti (Nikon, Tokyo, Japan) and analyzed by the NIS-Element software.

For human cervical cancer in vivo experiment, the first intra-tumoral injection (7 μg/tumor) of mimic-miR-122*, si-E6 or si-Scr was performed after the tumors were formed (Day 0). The intra-tumoral injections were performed every second day. Twenty tree days after the treatment, animals were euthanized and their s.c. lesions were resected and either immediately snap-frozen in liquid nitrogen for RNA and protein extraction or fixed with 4% paraformaldehyde for histological examination.

Tumor width (W) and length (L) were measured with caliper and tumor volume (V) was calculated with the formula $W^2*(L*0.5)$.

Statistical Analysis

Data are means±standard deviation (SD). Statistical significance was calculated using Students' t-test. A two-tailed $P<0.05$ was taken to indicate a statistically significant difference. The one-way analysis of variance (ANOVA) was performed using the GraphPad Prism software.

Bioinformatical Analysis

The 3'UTR of human and mouse mdm2 gene were obtained from the NCBI database (www.ncbi.nlm.nih.gov). The sequences of miR-18a, miR-122, miR-122* and miR-124 were obtained from mirBase database (www.mirbase.org) and microRNA target prediction was performed using the EMBL target prediction tool (www.ebi.ac.uk/enright-srv/microcosm/htdocs/targets/v5).

Example 1: miR-122* is Expressed in Parallel to miR-122

Figure 1B:
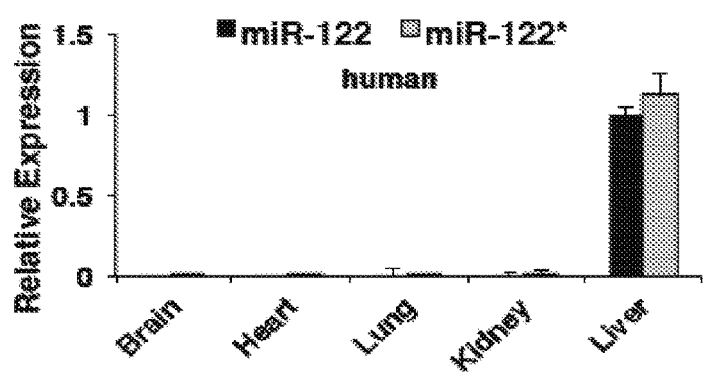
Figure 1C:
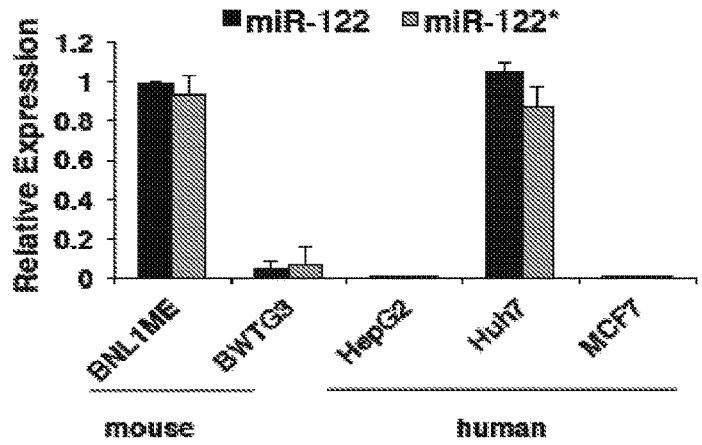
Figure 1D:
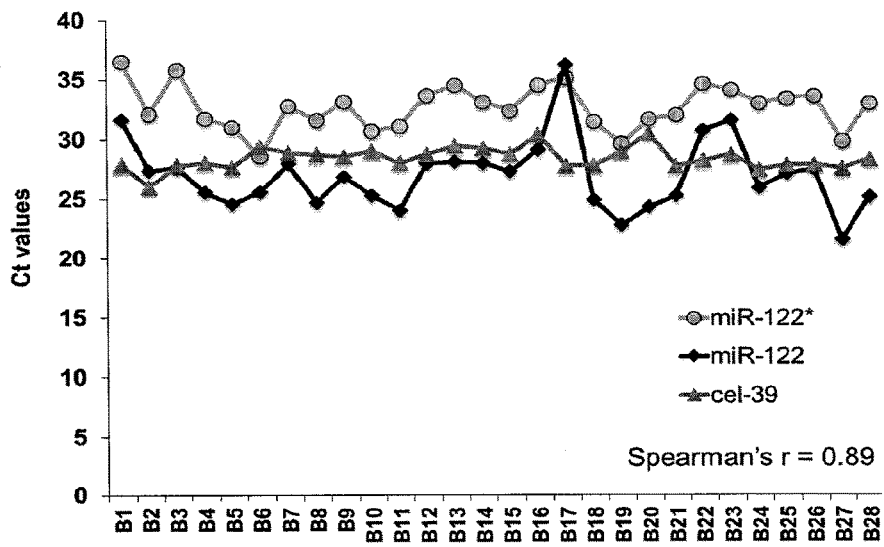
Figure 1E:
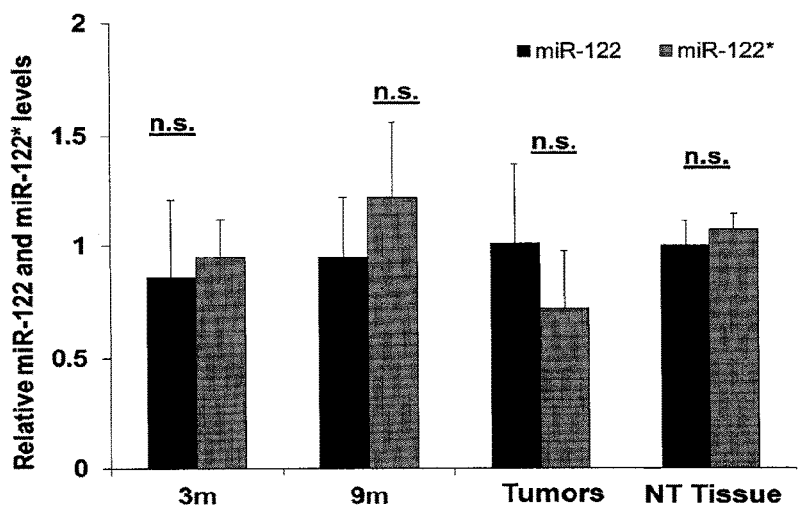
Figure 1F:
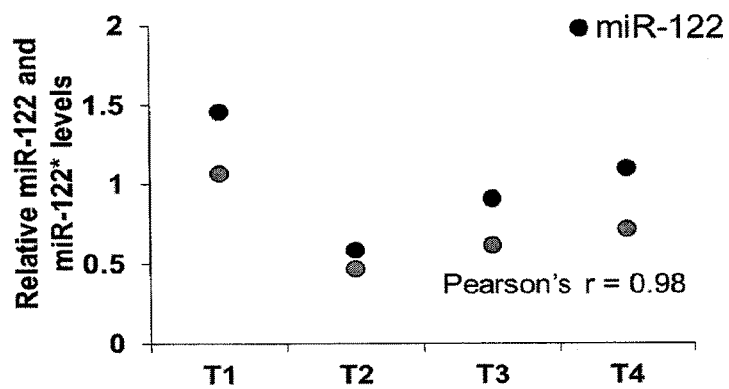

The relative expression of miR-122* and miR-122 was determined by quantitative RT-PCR (qRT-PCR) analysis in various mice and brain tissues or cell lines. The comparative results are presented in FIGS. 1A-F. FIG. 1A-B show the relative expression of miR-122* in various tissues (brain, heart, lung, kidney, and liver) obtained from mice and human, respectively. FIG. 1C—a shows the relative expression levels of miR-122* in the human cancer cell lines (HepG2, Huh7 and MCF 7) and mouse cancer cell lines (BNL1ME and BWTG3). Expression was normalized to RNU6 (mice) and RNU44 (human). FIG. 1D—shows the relative expression of mir-122, miR-122* and cel-39 in human blood serum samples obtained from cancer patients. FIG. 1E—shows the relative expression of mir-122 and miR-122* in samples obtained from MDR2 KO mice liver (pre-cancerous 3 months (3 m), 9 months (9 m), tumors, or non-tumorous tissue (NT), at different time points. FIG. 1F shows the relative expression of mir-122 and miR-122* in samples obtained from MDR2 KO mice liver tumors (T).

All together, the results demonstrate that the expression of miR-122* parallels that of miR-122 microRNA, in various mouse and human tissues, under different biological conditions.

Example 2: Inhibition of miR-122 Results in Elevated miR-122* Levels

Figure 2A:
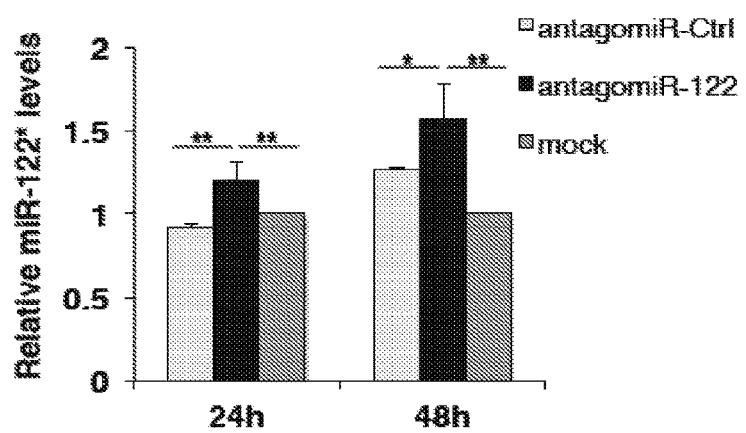
FIGS. 2A-B Bar graphs showing relative expression of miR-122* following inhibition of miR-122 by antagomiR-122, in-vitro and in-vivo, as determined by quantitative RT-PCR (qRT-PCR) analysis.
Figure 2B:
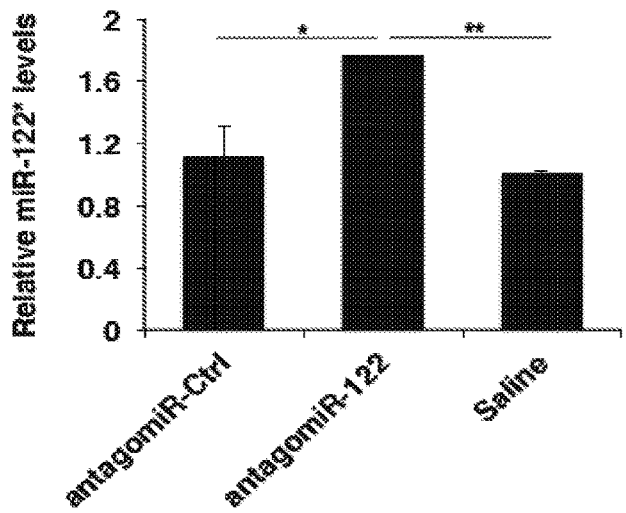
Figure 2C:
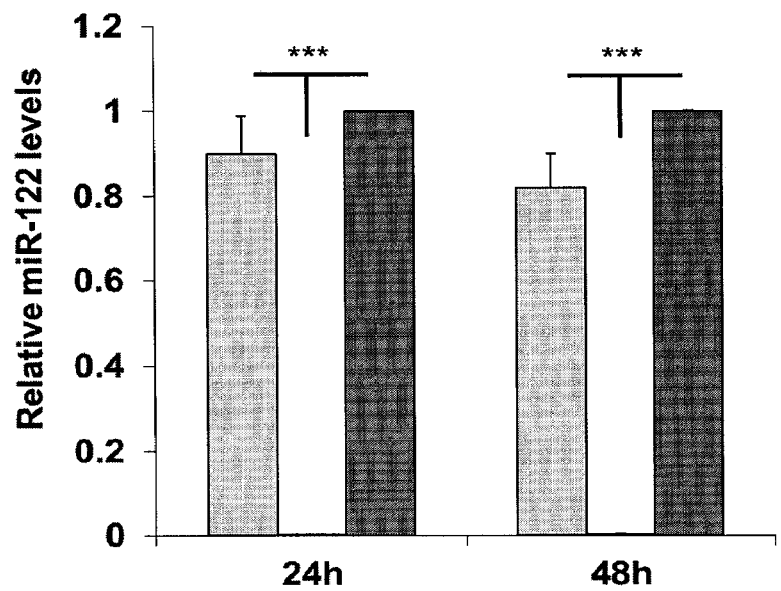
FIGS. 2C-D Bar graphs showing relative expression of miR-122 following inhibition of miR-122 by antagomiR-122, in-vitro and in-vivo, as determined by quantitative RT-PCR (qRT-PCR) analysis.
Figure 2D:
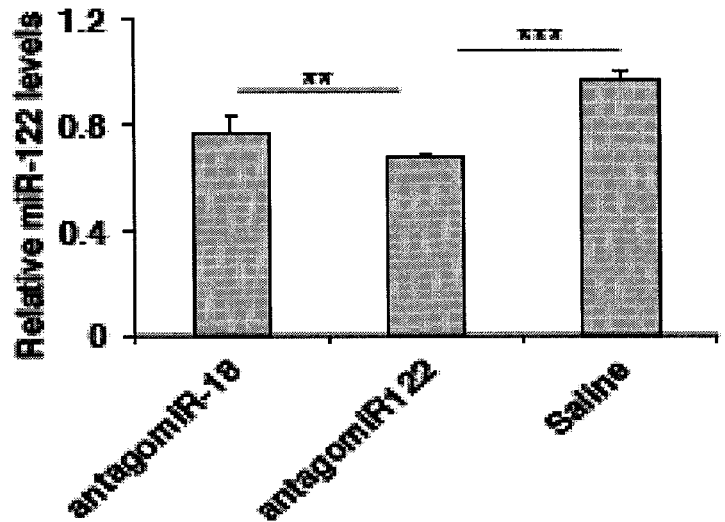

The relative expression of miR-122* following inhibition of miR-122 by specific antagomiR-122, in-vitro and in-vivo, was determined by quantitative RT-PCR (qRT-PCR) analysis. Such antisense technologies are used for in vivo miR-122 silencing. However, the therapeutic inhibition of miR-122 may result in an undesirable over-expression of miR-122 target genes, which are essential for growth suppression. As exemplified herein, reducing the level of miR-122 by antagomiR, resulted in an increase of miR-122*. The results are presented in FIGS. 2A-D. FIG. 2A shows Relative miR-122* expression in Huh7 cells treated with Control antagomiR (antagomiR-ctrl), miR-122 antagomiR (antagomiR-122), or mock treated, at 24 hours and 48 hours after treatment. FIG. 2B shows the relative miR-122* expression in murine liver following treatment with Ctrl antagomiR (antagomiR-ctrl), miR-122 antagomiR (antagomiR-122), or saline treatment. FIGS. 2C-D show the corresponding relative expression of miR-122 following inhibition of miR-122 by antagomiR-122, in-vitro and in-vivo, as determined by quantitative RT-PCR (qRT-PCR) analysis in Huh7 cells (FIG. 2C) and murine liver (FIG. 2D). All together, the results show that reducing the level of miR-122 by antagomiR, resulted in an increase of miR-122*.

Example 3: Mdm2 is a Target of miR-122* for Post Transcriptional Repression

Figure 3B:
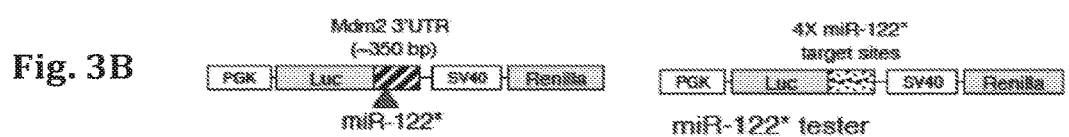

Mdm2, was identified as a target gene of miR-122*. The 3'UTR region of MDM 2 comprises a sequence which is of sufficient complementary to the miR-122* sequence. (FIG. 3A). To test the effect of miR-122* on Mdm2, several constructs were constructed, as detailed above and schematically illustrated in FIG. 3B. Left hand panel of FIG. 3B shows a schematic illustration of a construct comprising a fragment from the 3' UTR of Mdm2 gene (Mdm2 3'UTR), having a binding sequence of miR-122* (indicated by a triangle). The construct further includes a PGK promoter sequence upstream to a Luciferase (LUC) reporter encoding sequence (LUC), and a SV40 promoter sequence (SV40)' located downstream to the mdm2 3'-UTR sequence and upstream to a *Renilla* reporter encoding sequence. Left hand panel of FIG. 3B shows a schematic illustration of a miR-122* tester construct comprising a stretch of 4 consecutive binding (target) sites of miR-122* (4×miR-122*).

Figure 3C:
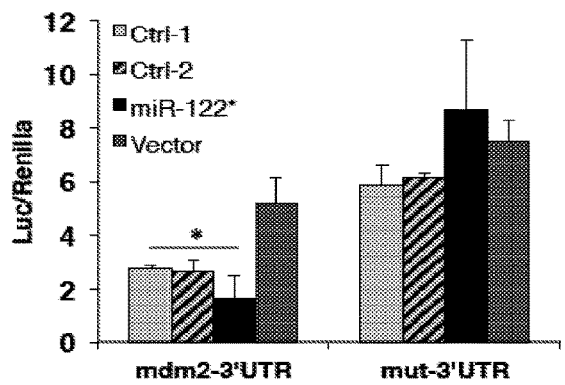
Figure 3D:
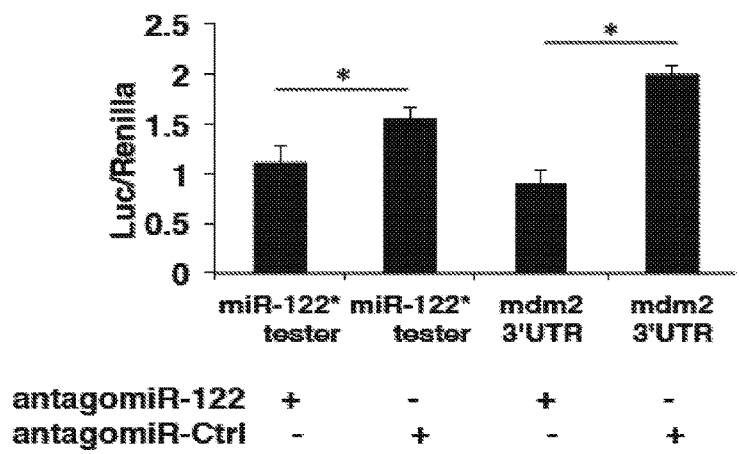
Figure 3E:
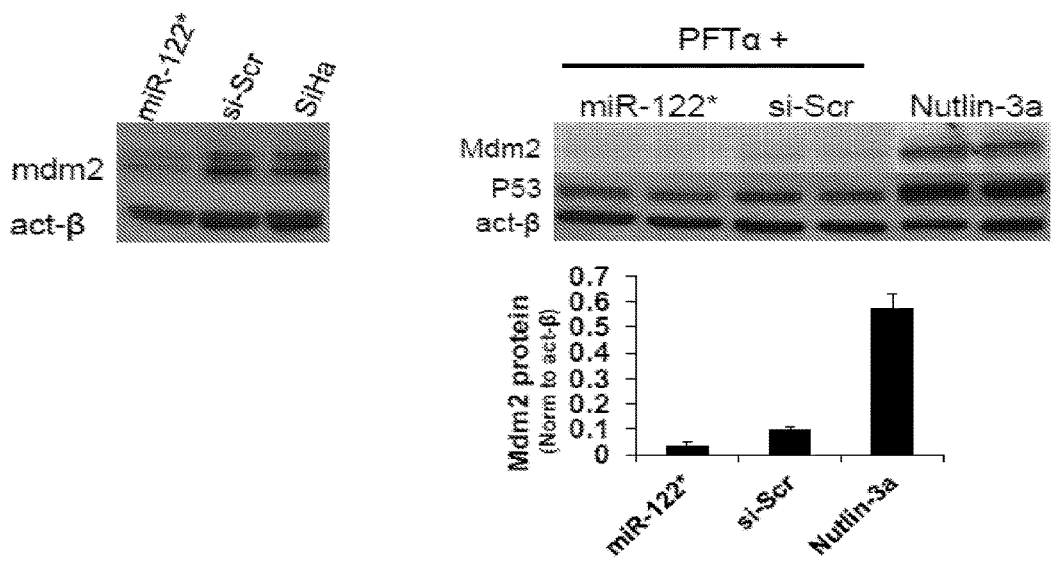

The constructs were transfected to test cells, as described above and luciferase activity (i.e., activation of the constructs) in the cells was determined FIG. 3C—shows the results of luciferase assay in HEK293 cells transfected with the mdm2-3UTR construct, or a similar construct harboring a point mutation in the miR-122* binding site within the mdm2-3'UTR (mut-3'UTR) and further transfected with either control siRNA molecules (Ctrl 1 (si-GFP), Ctrl-2 (si-Scr), miR-122* molecule (Sequences of Ctrl siRNAs and miR-122* are listed in Table 3), or empty vector (as detailed below). FIG. 3D—shows the results of a luciferase assay in Huh7 cells transfected with the miR-122* tester construct or the mdm2-3'-UTR construct, and either transfected with a specific mir-122 antagomiR (antagomiR-122) or a control antagomiR (antagomiR-Ctrl). FIG. 3E—show Western Blot analysis showing suppression of Mdm2 upon miR-122* overexpression in human cervical cancer SiHa cells (left) and HCC cells (right). HepG2 cells treated with miR-122* or control miR-Scramble (si-Scr) in the presence of Pifitrin α (PFTα) which inhibits P53. The cells were treated with Nutlin-3a to show the ability of p53 to accumulate in HepG2 cell line. Nutlin-3a is a chemical inhibitor of mdm2 protein, which disrupts its interaction with p53, leading to the stabilization and accumulation of p53.

Altogether, the results show that miR-122* can bind to and affect Mdm2 expression levels in target cells.

Figure 4A:
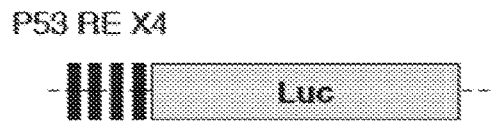
FIG. 4A-D—Activity of miR-122* results in elevated p53 levels in-vivo and in-vitro.
Figure 4B:
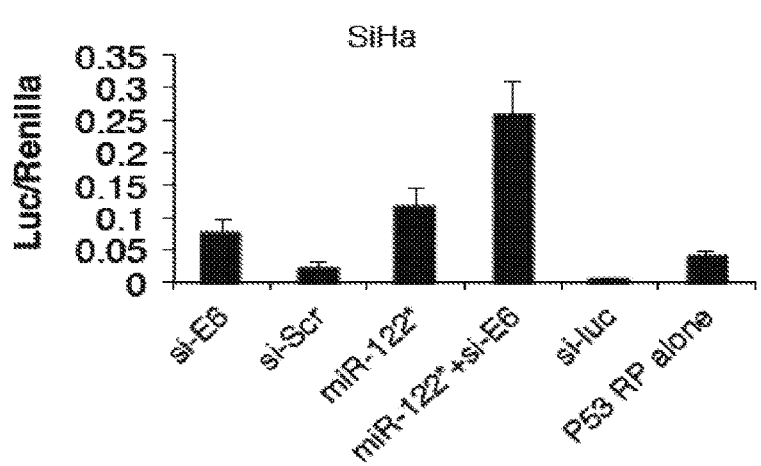
Figure 4C:
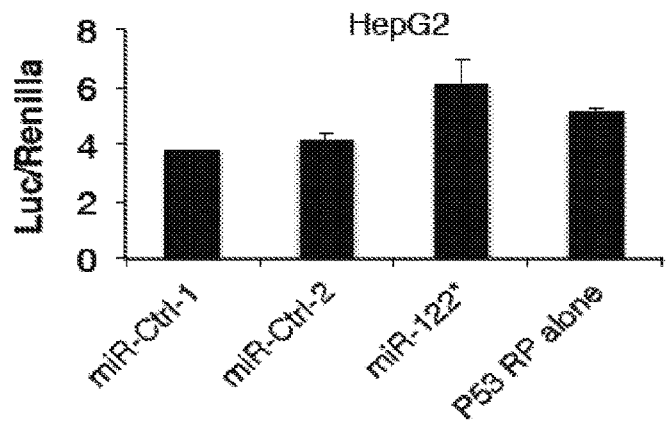
Figure 4D:
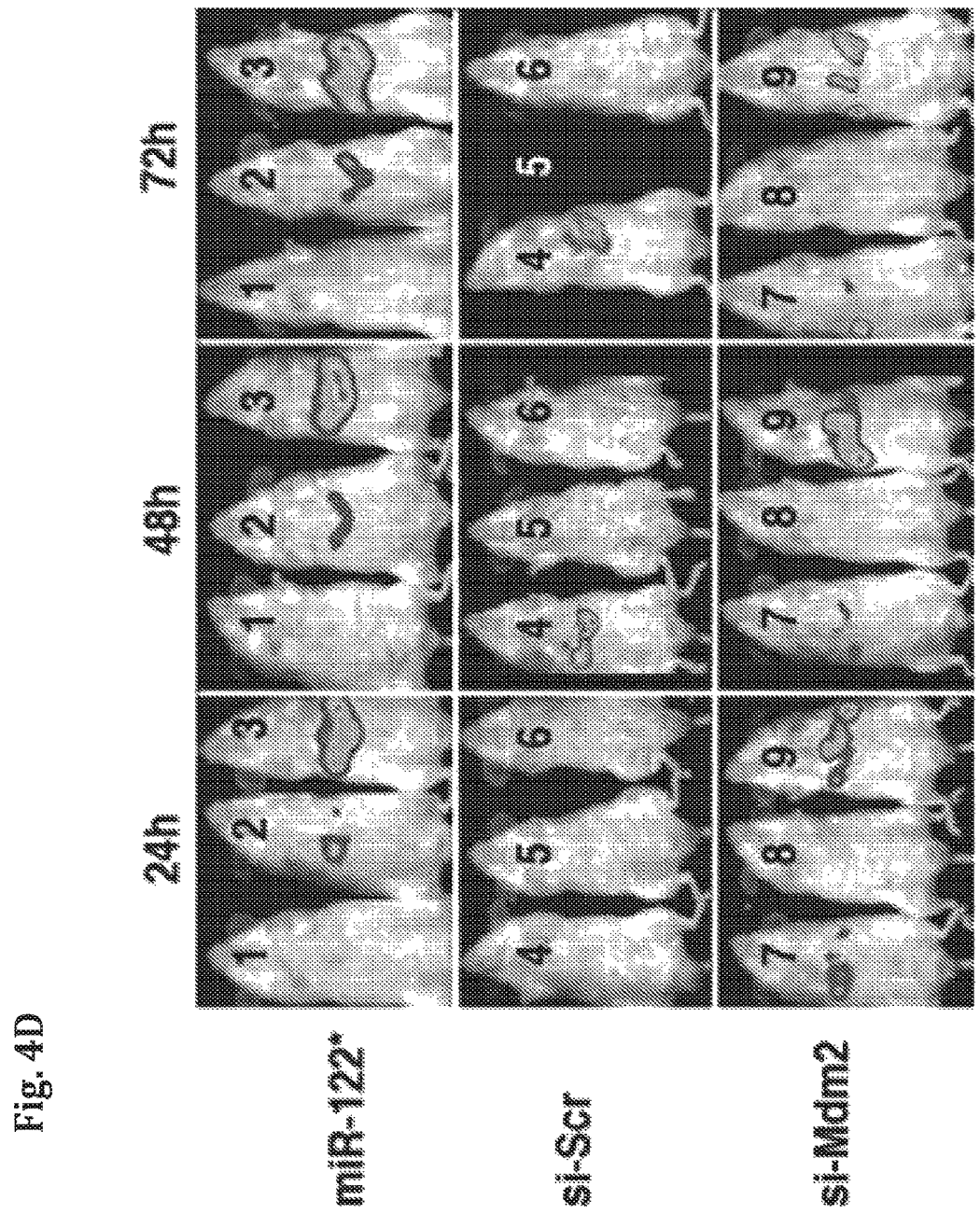

Example 4: Activity of miR-122* Results in Elevated p53 Levels In-Vivo and In-Vitro To test the effect of expression of miR-122* on p53 in vitro and in-vivo, several constructs were constructed, as detailed above and schematically illustrated in FIG. 4A. The p53 reporter construct includes a stretch of 4 consecutive p53 responsive element (RE) sequences (p53REX4) from the p21 native promoter, located upstream to a reporter luciferase expression sequence. This reporter plasmid was tested in various target cells under various experimental conditions. The results shown in FIG. 4B demonstrate the relative Luciferase/*Renilla* activity in siHA cells transfected with the p53REX4 reporter construct and with either: siRNA molecule directed against E6 gene (si-E6); a control siRNA molecule against Scr (si-Scr); miR-122* molecule (miR-122*); a combination of si-E6 and miR-122* molecules; Control siRNA against luciferase (si-Luc); or no other molecule (P53RP alone). The results shown in FIG. 4C demonstrate the relative Luciferase/*Renilla* activity in HepG2 cells (harboring a wt p53), transfected with the p53REX4 construct and with either: ctrl siRNA molecules, miR-122* molecule, or no other molecule (P53RP alone). The in-vivo results shown in FIG. 4D are of luciferase expression in liver of mice that have been injected with the p53REX4 DNA construct, by tail vain injection, along with miR-122* molecule (miR-122*) or control si-RNA molecules (si-Scr or si-Mdm2) The images were taken using IVIS (Caliper, lifeSciencse), at the indicated time points (hours after injection).

Altogether, the results demonstrate the expression of miR-122* in the target cells or in-vivo, results in enhanced expression and/or activity and/or stabilization of p53 protein.

Figure 5:
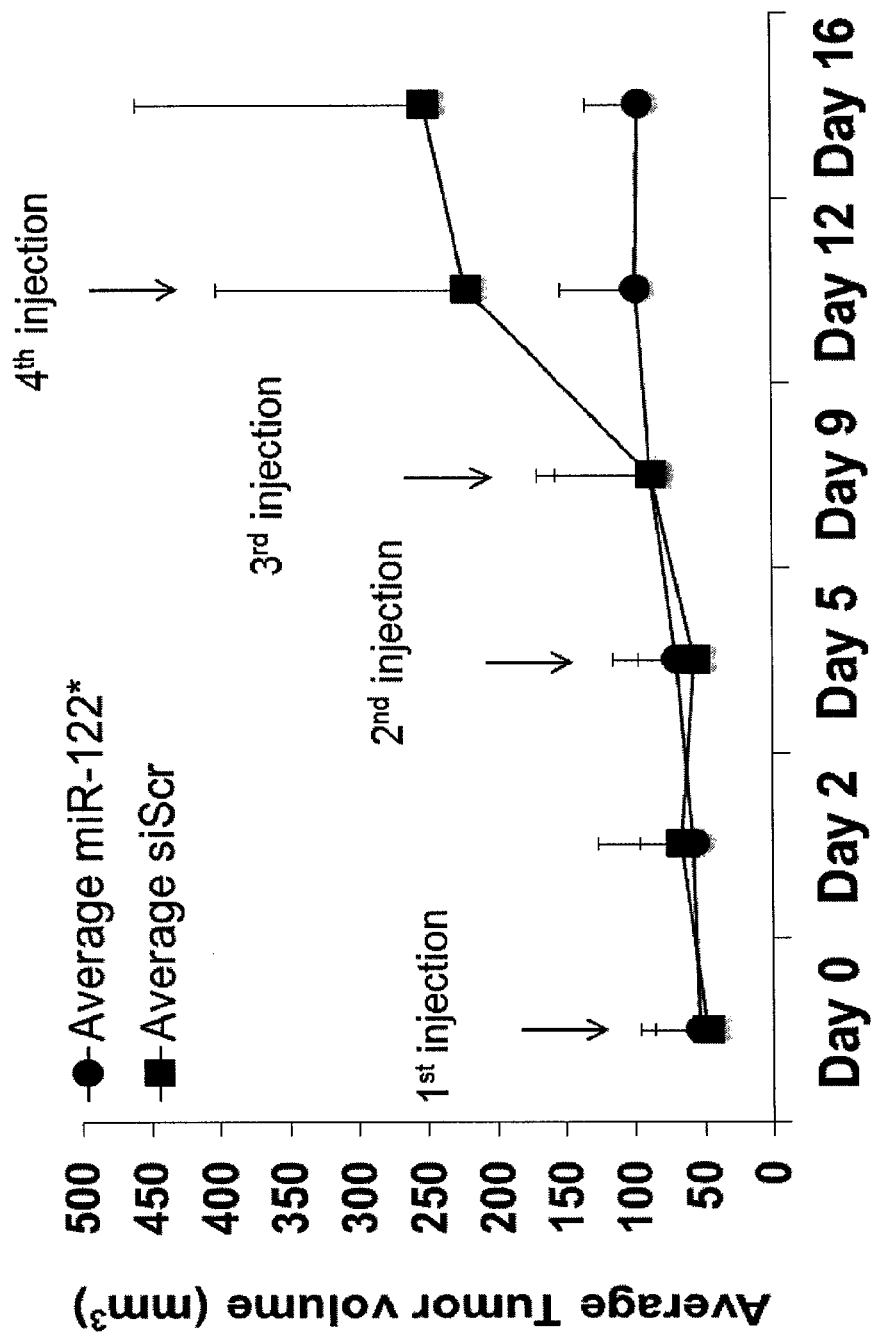
FIG. 5. Inhibitory effect of miR122* on tumor growth in a nude mouse xenograft model. The bar graph shown in FIG. 5 illustrates the in-vivo growth rate of subcutaneous tumors (Average tumor Volume (mm$^3$)) in nude mice injected with miR-122* molecule or a control siRNA molecule (si-Scr). The subcutaneous tumors were generated by injection of 1.5*10$^6$ HepG2 cells into the right flank of nude mice. After the tumors were formed (day 0), intra-tumoral injection of miR-122* or si-Scr was performed (day 0) and was repeated 3 more times (2$^{nd}$ injection of Day 5, 3$^{rd}$ injection on Day 9 and 4$^{th}$ injection of Day 12). Tumor width (W) and Length (L) were measured with calliper and tumor volume was calculated (W$^2$*(L*0.5)).

Example 5: Inhibitory Effect of miR122* on Tumor Growth in a Nude Mouse Xenograft Model To test the in-vivo effect of miR-122* on tumor growth reduction, direct injections of miR-122* into subcutaneous masses of human hepatocellular carcinoma (HCC) in nude mice, was performed. FIG. 5 illustrates the in-vivo growth rate of subcutaneous tumors (Average tumor Volume (mm$^3$)) in nude mice injected with miR-122* molecule or a control siRNA molecule (si-Scr). The subcutaneous tumors were generated by injection of 1.5*10$^6$ HepG2 cells into the right flank of nude mice. After the tumors were formed (day 0), intra-tumoral injection of miR-122* or si-Scr was performed (day 0) and was repeated 3 more times (2$^{nd}$ injection of Day 5, 3$^{rd}$ injection on Day 9a and 4$^{th}$ injection of Day 12). Tumor width (W) and Length (L) were measured with calliper and tumor volume was calculated (W$^2$*(L*0.5)).

The striking results demonstrate the in-vivo effect of mir-122* as a tumor suppressor that can affect tumor growth.

Example 6: Activity of miR-122* Leads to Inhibition of Cancer Cells Growth

Figure 6A:
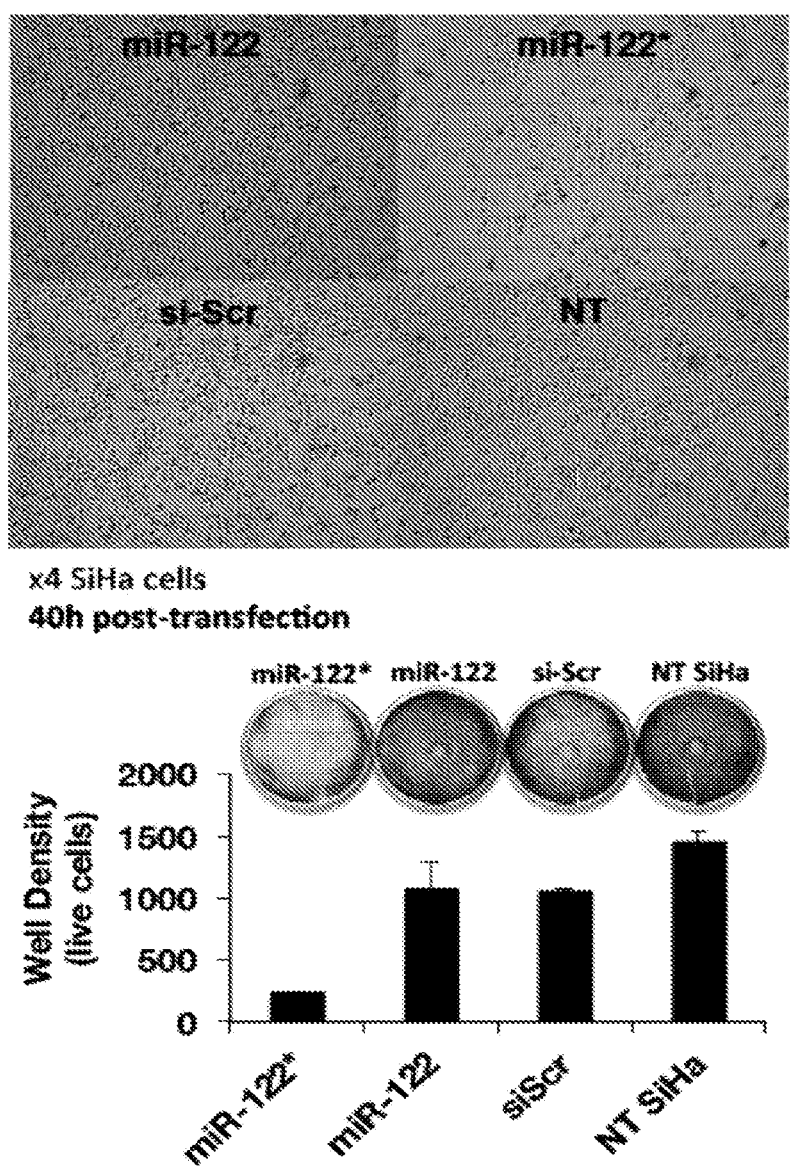
Figure 6C:
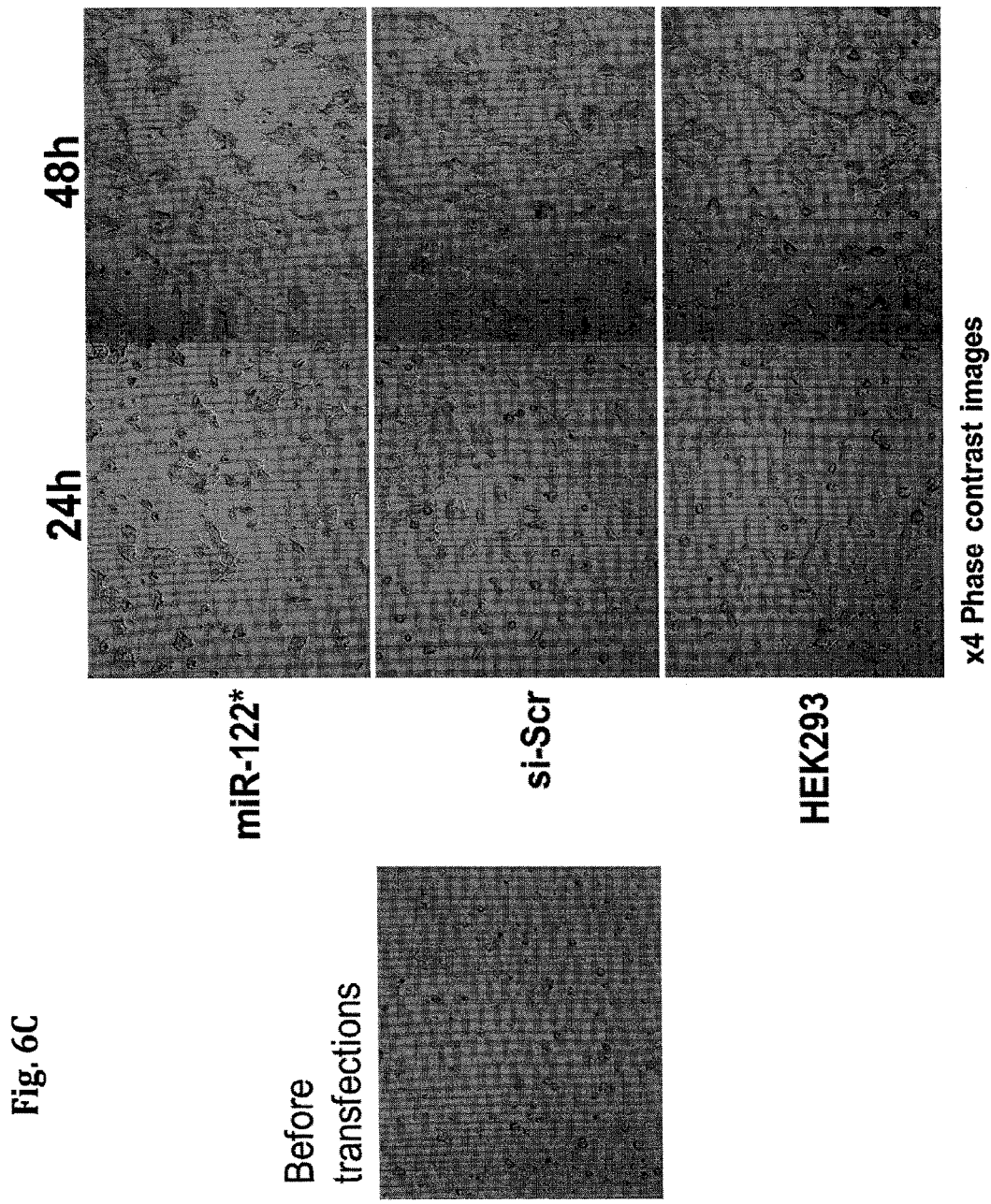

To test the effect of miR-122* as a cervical cancer treatment, SiHa cells, a cervical cancer cell line harboring one genomic copy of HPV16/cell was used as an in vitro model. Treatment of these cells as well as HepG2 cells (human hepatocellular carcinoma cells) with miR-122*, as detailed above resulted in cancer cell growth inhibition. FIG. 6A shows siHa cells that were transfected with: miR-122* molecule, or mir-122 molecule, or si-Scr molecule, or not treated (NT), 40 hours post transfection, the cells were visualized by phase contrast microscope and stained by crystal violet solution. The pictograms are shown in the upper panel of FIG. 6A (4× magnification). The bar graphs in the lower panel of FIG. 6A shows quantification of the results, illustrating the well density (live cells) in the transfected cells (miR-122*, mir-122 and si-Scr), or in the control, non-treated cells. Error bars indicated mean+SD. FIG. 6B shows He G2 cells that were transfected with either: miR-122* molecule, or control siRNA (si-Scr), and where indicated were further treated with PFT-α (inhibitor of p53). In addition, non treated cells (HepG2, UT) or cells not transfected but treated with PFTα, were used. The various cells were analyzed by How cytometry analysis (FACS) of PI-stained cells (i.e. apoptotic rate was determined). FIG. 6C—shows HEK293 cells, non treated or transfected with miR-122* molecule or si-Scr molecule (si-Scr), 24 hours and 48 hours after transfection. The pictograms (4× magnification, phase contrast images) show the cell density of the cells before transfection, 24 hours and 48 hours after transfection.

The results demonstrate the marked effect of miR-122* in the cancer cells (siHA and Hep G2) on cell growth. The expression of miR-122* in the cells results in increased cell growth inhibition.

Figure 7A:
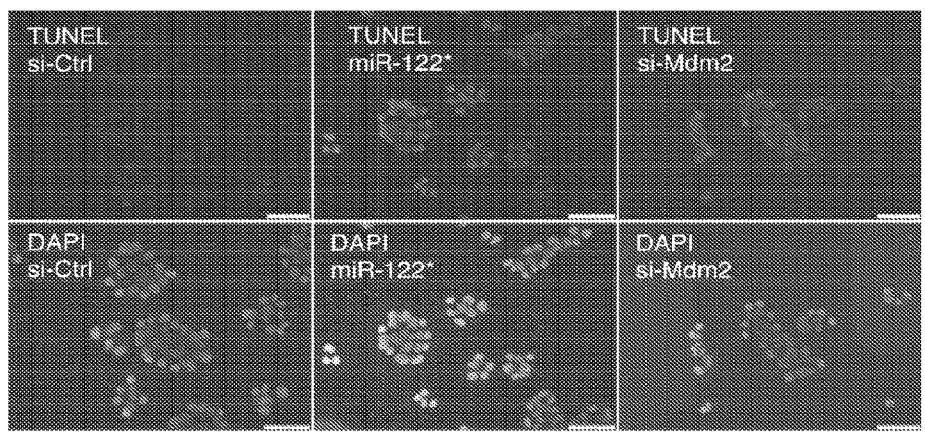
FIGS. 7A-F— Activity of miR-122* leads to inhibition of cancer cell growth in vitro and in vivo.

Example 7: The Activity of miR-122* Leads to Inhibition of Cancer Cell Growth In Vitro and In Vivo To further demonstrate the in-vitro and in-vivo activity of miR-122* in inhibition of cancer cell growth, the viability of HepG2 cells was tested 40 hours after introduction of miR-122*. In the results shown in FIG. 7A, increased TUNEL signal in HepG2 cells 40 h after introduction of miR-122* were observed, thus confirming the pro-apoptotic activity of miR-122*.

Figure 7B:
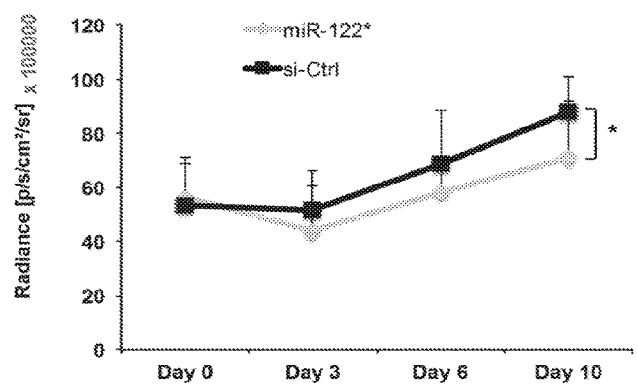
Figure 7C:
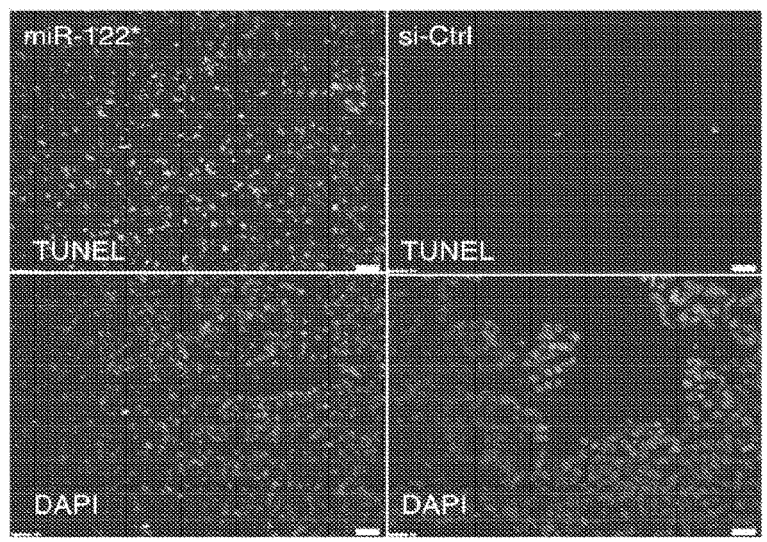
Figure 7D:
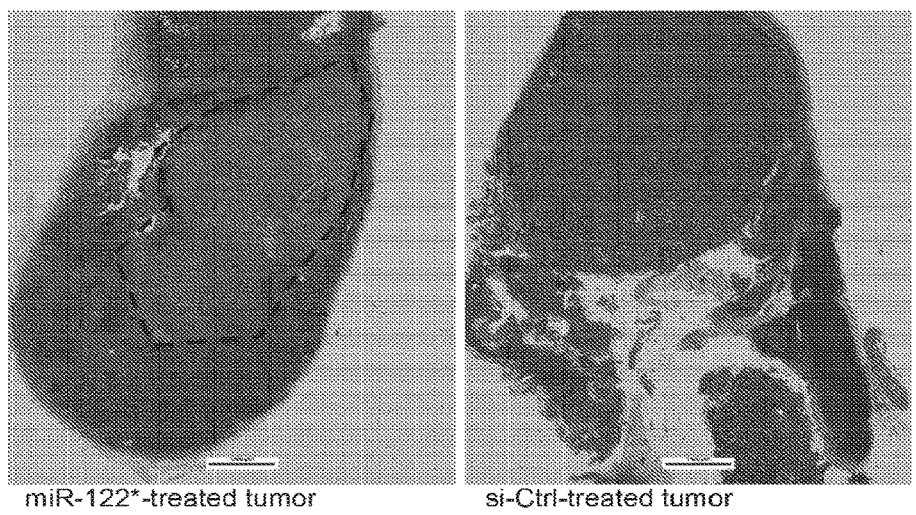
Figure 7E:
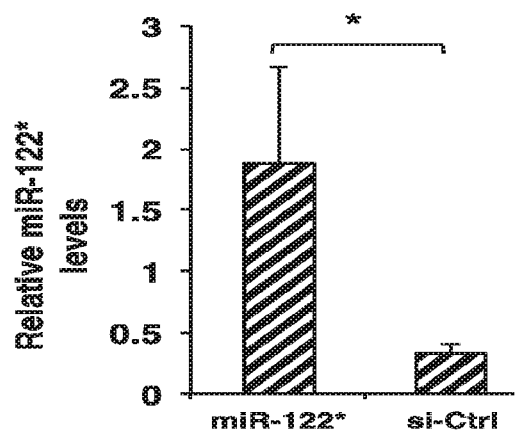
Figure 7F:
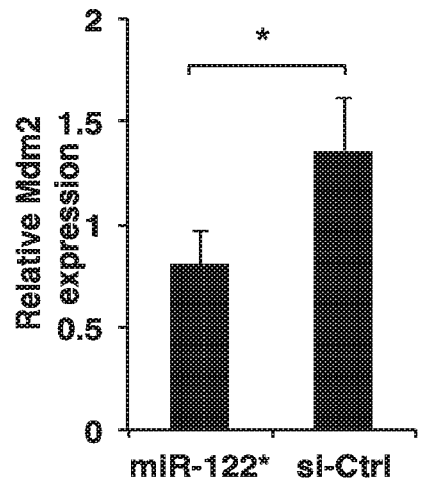

Next, HepG2 cells stably expressing a luciferase gene were implanted subcutaneously into the flanks of NOD-.SCID immunocompromised mice. Direct injections of miR-122* into established tumors, significantly inhibited tumor growth relative to the control miRNA, as demonstrated in FIG. 7B. TUNEL assays performed 3 days after the first intratumoral miR-122* injection, revealed extensive apoptosis, as demonstrated in the pictograms shown in FIG. 7C. Moreover, miR-122*-treated tumors contained large necrotic areas, as demonstrated in FIG. 7D. Testing the expression of Mdm2 one day after the last miR-122* injection, reveals a negative correlation between Mdm2 expression in the tumors and miR-122* levels, as demonstrated in the Graphs shown in FIGS. 7E and 7F, respectively.

Figure 8A:
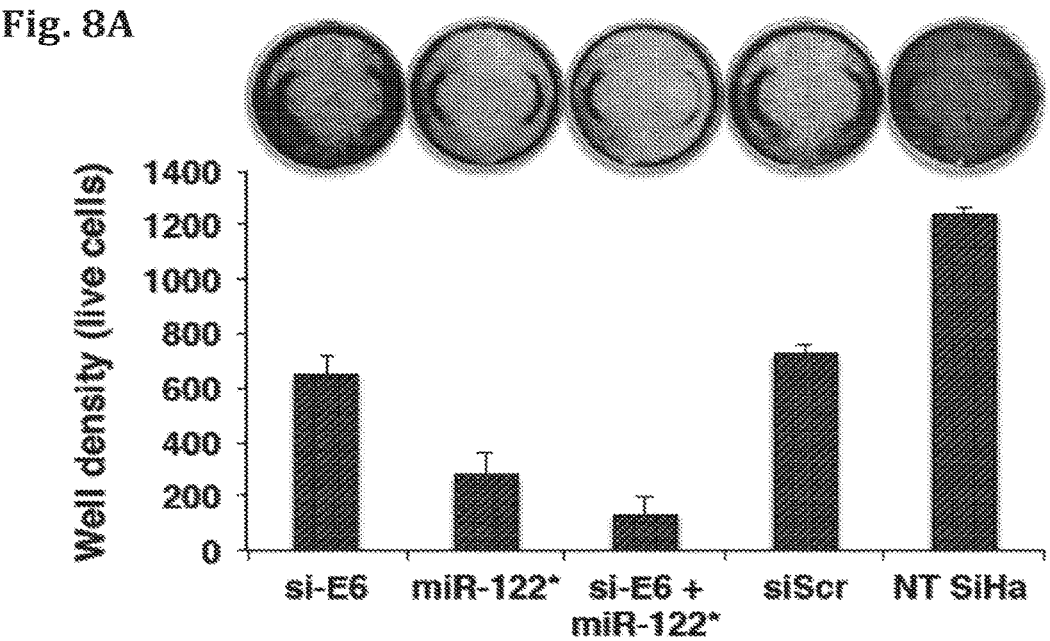
FIGS. 8A-E. Combined activity of miR-122* and siRNA against E6 inhibits cervical cancer cells growth in-vitro and in-vivo. SiHa cells were transfected with either siRNA molecule against E6 gene (si-E6), miR-122* molecule (miR-122*), a combination of si-E6 and miR-122*, a control siRNA (siScr), or not treated (NT). Five days post transfection, the cells were stained by Crystal violet solution, and well density, which corresponds to the number of live cells was determined. The upper panel of FIG. 8A shows pictograms of the test cells and the lower panel of FIG. 8A shows bar graphs quantification of the results illustrating the well density under the various experimental conditions.

Example 8: miR-122* in Combination with siRNA Against E6 Gene Inhibits Cervical Cancer Cells Growth To test the combined effect of miR-122* expression and an agent directed against E6 gene, in cervical cancer cells, SiHa cells were transfected with either: siRNA molecule against E6 gene (si-E6), miR-122* molecule (miR-122*), a combination of si-E6 and miR-122*, a control siRNA (siScr), or not treated (NT). Five days post transfection, the cells were stained by Crystal violet solution, and well density, which corresponds to the number of live cells was determined. The results shown in FIG. 8A demonstrate that combined treatment of SiHa cells with miR-122* and si-E6 induces cell death even more intensively than si-E6 treatment alone, which led only to a modest growth inhibitory response (FIG. 8A). Furthermore, as detailed in Example 4, above, this treatment efficiently induced the activity of p53, as determined by using a reporter plasmid carrying the P21 promoter, which harbours a p53 responsive elements.

Figure 8B:
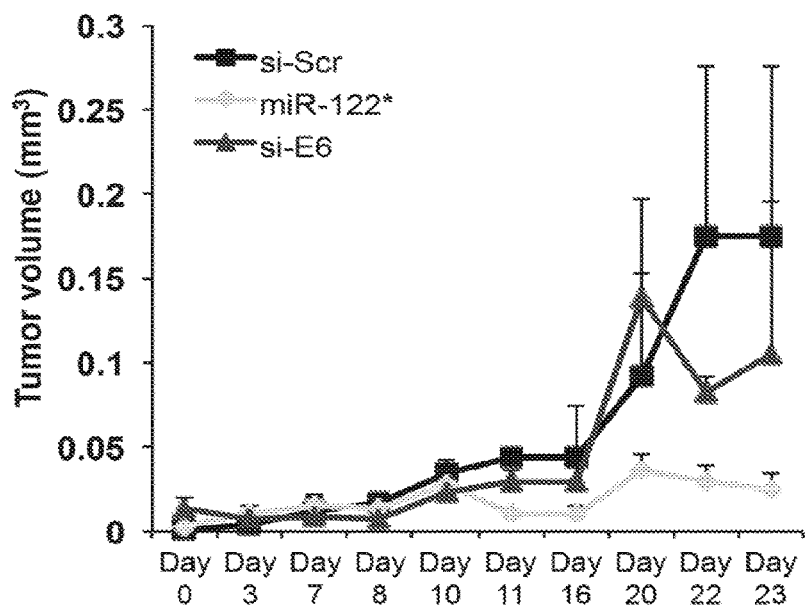
Figure 8C:
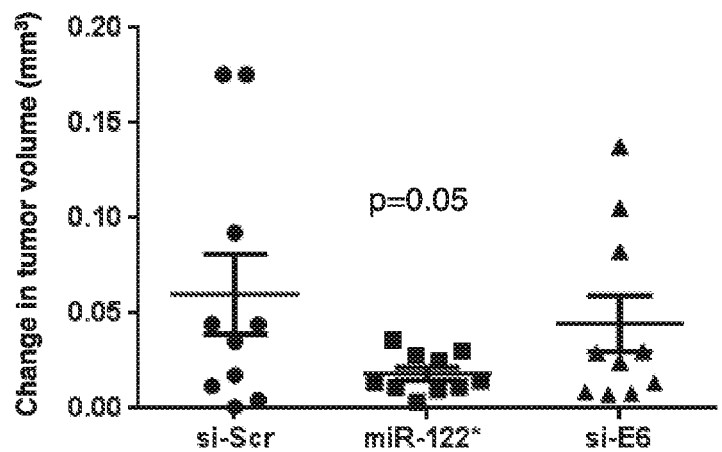
Figure 8D:
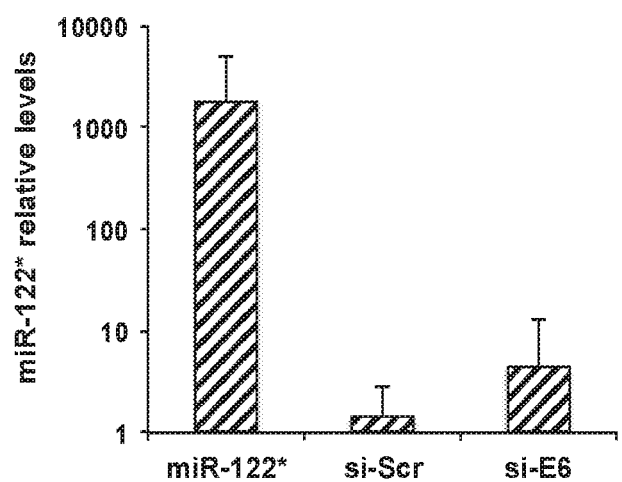
Figure 8E:
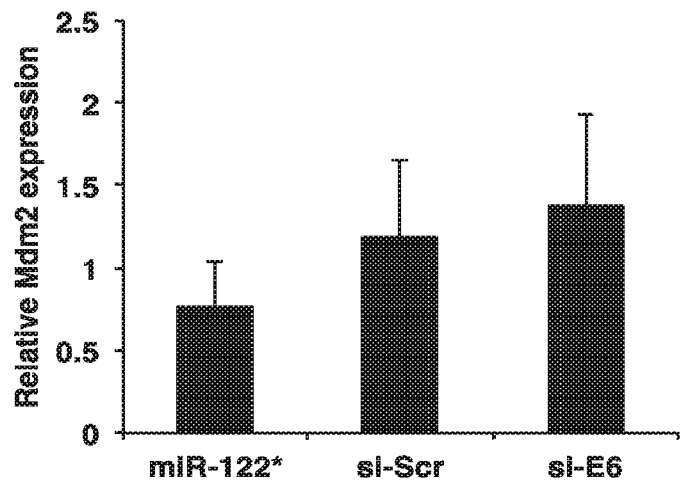

Next, SiHa cells were implanted subcutaneously into the flanks of NOD.SCID mice. The generated tumors were treated with miR-122*, si-E6 (siRNA against the viral oncoprotein E6) or control miRNA molecules. Direct injections of miR-122* into established tumors resulted in a slight inhibition of tumor growth relative to the control treatments, as demonstrated in FIG. 8B. One way analysis of variance (ANOVA) was performed to compare the change in tumor volume within each treatment group 23 days after the first injection (FIG. 8C). This test shows that direct injections of miR-122* into the tumor can inhibit tumor development. Further, as shown in FIG. 8D, synthetic miR-122* is capable of entering tumor cells without carrier molecules.

Altogether, the results show that treatment of cervical cancer cells both in-vitro and in-vivo in the context of an organism, with si-E6 can be enhanced and sustained by the addition of miR-122*. The combined siRNA-miRNA-based treatment provides enhanced results as compared to currently used methods for treating similar conditions.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of treating cancer in a subject in need thereof, the method comprising administering a miR-122* polynucleotide molecule, comprising at least one modified nucleotide, thereby treating cancer in the subject.

2. The method of claim 1, wherein the miR-122* molecule comprises the nucleotide sequence of SEQ ID NO: 1.

3. The method of claim 1, wherein cells of the cancer harbor a wild type p53.

4. The method of claim 1, wherein the cancer is a cervical cancer.

5. The method of claim 4, wherein the cancer originated from viral infection, wherein the viral infection is caused by Human Papilloma Virus (HPV), Hepatitis C Virus (HCV), or both.

6. The method of claim 1 further comprising administering an agent capable of reducing expression or activity of E6 gene product, E7 gene product or both.

7. The method of claim 6, wherein the agent is a polynucleotide molecule, selected from siRNA, miRNA, and antisense (AS) molecule.

8. The method of claim 6, wherein the agent is administered concomitantly with the miR-122* polynucleotide molecule.

9. A method for inducing cancer cell death, the method comprising introducing into the cancer cell a miR-122* polynucleotide molecule, wherein the polynucleotide molecule comprises at least one modified nucleotide.

10. The method of claim 9, wherein the miR-122* molecule comprises the nucleotide sequence of SEQ ID NO: 1.

11. The method of claim 9, wherein the cancer cell is harbored in a tissue or organism.

12. The method of claim 11, wherein the cancer cell is of hepatic origin or cervical origin.

* * * * *

SEQUENCE LISTING

```
<160> NUMBER OF SEQ ID NOS: 24

<210> SEQ ID NO 1
<211> LENGTH: 22
<212> TYPE: RNA
<213> ORGANISM: Artificial sequence
<220> FEATURE:
<223> OTHER INFORMATION: polynucleotide

<400> SEQUENCE: 1
aacgccauua ucacacuaaa ua                                              22

<210> SEQ ID NO 2
<211> LENGTH: 6
<212> TYPE: RNA
<213> ORGANISM: Artificial sequence
<220> FEATURE:
<223> OTHER INFORMATION: polynucleotide

<400> SEQUENCE: 2 acgcca                                                                 6

<210> SEQ ID NO 3
<211> LENGTH: 33
<212> TYPE: DNA
<213> ORGANISM: Artificial sequence
<220> FEATURE:
<223> OTHER INFORMATION: polynucleotide

<400> SEQUENCE: 3
tacccaggct ggagtgcagt ggcgtgatct tgg                                  33

<210> SEQ ID NO 4
<211> LENGTH: 6
<212> TYPE: DNA
<213> ORGANISM: Artificial sequence
<220> FEATURE:
<223> OTHER INFORMATION: polynucleotide

<400> SEQUENCE: 4 tggcgt                                                                 6
```

```
<210> SEQ ID NO 5
<211> LENGTH: 20
<212> TYPE: DNA
<213> ORGANISM: Artificial sequence
<220> FEATURE:
<223> OTHER INFORMATION: primer

<400> SEQUENCE: 5
accacagtcc atgccatcac                                                     20

<210> SEQ ID NO 6
<211> LENGTH: 20
<212> TYPE: DNA
<213> ORGANISM: Artificial sequence
<220> FEATURE:
<223> OTHER INFORMATION: primer

<400> SEQUENCE: 6
tccaccaccc tgttgctgta                                                     20

<210> SEQ ID NO 7
<211> LENGTH: 21
<212> TYPE: DNA
<213> ORGANISM: Artificial sequence
<220> FEATURE:
<223> OTHER INFORMATION: primer

<400> SEQUENCE: 7
cctcataaag gccaagaagg g                                                   21

<210> SEQ ID NO 8
<211> LENGTH: 52
<212> TYPE: DNA
<213> ORGANISM: Artificial sequence
<220> FEATURE:
<223> OTHER INFORMATION: primer

<400> SEQUENCE: 8
ctagaaacgc cattatcaca ctaaatcgaa cgccattatc acactaagag ct                 52

<210> SEQ ID NO 9
<211> LENGTH: 44
<212> TYPE: DNA
<213> ORGANISM: Artificial sequence
<220> FEATURE:
<223> OTHER INFORMATION: Primer

<400> SEQUENCE: 9
cttagtgtga taatggcgtt cgatttagtg tgataatggc gttt                          44

<210> SEQ ID NO 10
<211> LENGTH: 53
<212> TYPE: DNA
<213> ORGANISM: Artificial sequence
<220> FEATURE:
<223> OTHER INFORMATION: primer

<400> SEQUENCE: 10
ctagattagt gtgataatgg cgttcgattt agtgtgataa tggcgttcct gca                53

<210> SEQ ID NO 11
<211> LENGTH: 45
<212> TYPE: DNA
<213> ORGANISM: Artificial sequence
<220> FEATURE:
<223> OTHER INFORMATION: primer
```

```
<400> SEQUENCE: 11
ggaacgccat tatcacacta aatcgaacgc cattatcaca ctaat            45

<210> SEQ ID NO 12
<211> LENGTH: 30
<212> TYPE: DNA
<213> ORGANISM: Artificial sequence
<220> FEATURE:
<223> OTHER INFORMATION: primer

<400> SEQUENCE: 12
acctctgagc tcatcctttta caccaactcc                            30

<210> SEQ ID NO 13
<211> LENGTH: 30
<212> TYPE: DNA
<213> ORGANISM: Artificial sequence
<220> FEATURE:
<223> OTHER INFORMATION: primer

<400> SEQUENCE: 13
gatgactcta gaccaagcta attgggaggc                             30

<210> SEQ ID NO 14
<211> LENGTH: 23
<212> TYPE: RNA
<213> ORGANISM: Artificial sequence
<220> FEATURE:
<223> OTHER INFORMATION: primer
<220> FEATURE:
<221> NAME/KEY: modified_base
<222> LOCATION: (1)..(1)
<223> OTHER INFORMATION: phosphorothioate linkage
<220> FEATURE:
<221> NAME/KEY: modified_base
<222> LOCATION: (2)..(2)
<223> OTHER INFORMATION: phosphorothioate linkage
<220> FEATURE:
<221> NAME/KEY: modified_base
<222> LOCATION: (20)..(20)
<223> OTHER INFORMATION: phosphorothioate linkage
<220> FEATURE:
<221> NAME/KEY: modified_base
<222> LOCATION: (21)..(21)
<223> OTHER INFORMATION: phosphorothioate linkage
<220> FEATURE:
<221> NAME/KEY: modified_base
<222> LOCATION: (22)..(22)
<223> OTHER INFORMATION: phosphorothioate linkage
<220> FEATURE:
<221> NAME/KEY: modified_base
<222> LOCATION: (23)..(23)
<223> OTHER INFORMATION: cholesterol linked through a hydroxyprolinol
      linkage
<220> FEATURE:
<221> NAME/KEY: modified_base
<222> LOCATION: (23)..(23)
<223> OTHER INFORMATION: phosphorothioate linkage

<400> SEQUENCE: 14
acacacaaca cugucacauu cca                                    23

<210> SEQ ID NO 15
<211> LENGTH: 23
<212> TYPE: RNA
<213> ORGANISM: Artificial sequence
<220> FEATURE:
<223> OTHER INFORMATION: primer
<220> FEATURE:
<221> NAME/KEY: modified_base
```

```
<222> LOCATION: (1)..(1)
<223> OTHER INFORMATION: phosphorothioate linkage
<220> FEATURE:
<221> NAME/KEY: modified_base
<222> LOCATION: (2)..(2)
<223> OTHER INFORMATION: phosphorothioate linkage
<220> FEATURE:
<221> NAME/KEY: modified_base
<222> LOCATION: (20)..(20)
<223> OTHER INFORMATION: phosphorothioate linkage
<220> FEATURE:
<221> NAME/KEY: modified_base
<222> LOCATION: (21)..(21)
<223> OTHER INFORMATION: phosphorothioate linkage
<220> FEATURE:
<221> NAME/KEY: modified_base
<222> LOCATION: (22)..(22)
<223> OTHER INFORMATION: phosphorothioate linkage
<220> FEATURE:
<221> NAME/KEY: modified_base
<222> LOCATION: (23)..(23)
<223> OTHER INFORMATION: cholesterol linked through a hydroxyprolinol
      linkage
<220> FEATURE:
<221> NAME/KEY: modified_base
<222> LOCATION: (23)..(23)
<223> OTHER INFORMATION: phosphorothioate linkage

<400> SEQUENCE: 15
cuaucugcac uagaugcacc uua                                           23

<210> SEQ ID NO 16
<211> LENGTH: 19
<212> TYPE: RNA
<213> ORGANISM: Artificial sequence
<220> FEATURE:
<223> OTHER INFORMATION: primer
<220> FEATURE:
<221> NAME/KEY: modified_base
<222> LOCATION: (1)..(1)
<223> OTHER INFORMATION: phosphorothioate linkage
<220> FEATURE:
<221> NAME/KEY: modified_base
<222> LOCATION: (2)..(2)
<223> OTHER INFORMATION: phosphorothioate linkage
<220> FEATURE:
<221> NAME/KEY: modified_base
<222> LOCATION: (16)..(16)
<223> OTHER INFORMATION: phosphorothioate linkage
<220> FEATURE:
<221> NAME/KEY: modified_base
<222> LOCATION: (17)..(17)
<223> OTHER INFORMATION: phosphorothioate linkage
<220> FEATURE:
<221> NAME/KEY: modified_base
<222> LOCATION: (18)..(18)
<223> OTHER INFORMATION: phosphorothioate linkage
<220> FEATURE:
<221> NAME/KEY: modified_base
<222> LOCATION: (19)..(19)
<223> OTHER INFORMATION: cholesterol linked through a hydroxyprolinol
      linkage
<220> FEATURE:
<221> NAME/KEY: modified_base
<222> LOCATION: (19)..(19)
<223> OTHER INFORMATION: phosphorothioate linkage

<400> SEQUENCE: 16
ggcauucacc gcgugccuu                                                19

<210> SEQ ID NO 17
<211> LENGTH: 20
<212> TYPE: RNA
<213> ORGANISM: Artificial sequence
<220> FEATURE:
```

```
<223> OTHER INFORMATION: polynucleotide

<400> SEQUENCE: 17
uaaggcacgc ggugaaugcc                                              20

<210> SEQ ID NO 18
<211> LENGTH: 19
<212> TYPE: RNA
<213> ORGANISM: Artificial sequence
<220> FEATURE:
<223> OTHER INFORMATION: polynucleotide

<400> SEQUENCE: 18
gcugacccug aaguucauc                                               19

<210> SEQ ID NO 19
<211> LENGTH: 17
<212> TYPE: RNA
<213> ORGANISM: Artificial sequence
<220> FEATURE:
<223> OTHER INFORMATION: polynucleotide
<220> FEATURE:
<221> NAME/KEY: modified_base
<222> LOCATION: (17)..(17)
<223> OTHER INFORMATION: biotin

<400> SEQUENCE: 19
caccacauac cgcacgg                                                 17

<210> SEQ ID NO 20
<211> LENGTH: 19
<212> TYPE: RNA
<213> ORGANISM: Artificial sequence
<220> FEATURE:
<223> OTHER INFORMATION: polynucleotide

<400> SEQUENCE: 20
uccauaugcu guaugugau                                               19

<210> SEQ ID NO 21
<211> LENGTH: 19
<212> TYPE: RNA
<213> ORGANISM: Artificial sequence
<220> FEATURE:
<223> OTHER INFORMATION: polynucleotide

<400> SEQUENCE: 21
cuuacgcuga guacuucga                                               19

<210> SEQ ID NO 22
<211> LENGTH: 25
<212> TYPE: RNA
<213> ORGANISM: Artificial sequence
<220> FEATURE:
<223> OTHER INFORMATION: polynucleotide

<400> SEQUENCE: 22
aggcuuggau gugccugaug gcaaa                                        25

<210> SEQ ID NO 23
<211> LENGTH: 22
<212> TYPE: RNA
<213> ORGANISM: Artificial sequence
<220> FEATURE:
<223> OTHER INFORMATION: polynucleotide
<220> FEATURE:
<221> NAME/KEY: modified_base
```

```
<222> LOCATION: (22)..(22)
<223> OTHER INFORMATION: biotin

<400> SEQUENCE: 23
aacgccauua ucacacuaaa ua                                                22

<210> SEQ ID NO 24
<211> LENGTH: 18
<212> TYPE: RNA
<213> ORGANISM: Artificial sequence
<220> FEATURE:
<223> OTHER INFORMATION: polynucleotide

<400> SEQUENCE: 24
aucacacuau uaccgcaa                                                     18
```